United States Patent [19]
Steinberg et al.

[11] Patent Number: 6,025,326
[45] Date of Patent: *Feb. 15, 2000

[54] COMPOSITIONS AND METHODS FOR THE PREVENTION AND TREATMENT OF ORAL MUCOSITIS

[75] Inventors: Deborah A. Steinberg, Saratoga; De Hwa Chao; David J. Loury, both of San Jose; Roger Cherng Fu; Chee Liang Gu, both of Saratoga; Conway C. Chang, San Francisco; John C. Fiddes, Palo Alto, all of Calif.

[73] Assignee: IntraBiotics Pharmaceuticals, Inc., Mountain View, Calif.

[ * ] Notice: This patent is subject to a terminal disclaimer.

[21] Appl. No.: 08/752,853

[22] Filed: Nov. 21, 1996

Related U.S. Application Data

[62] Continuation-in-part of application No. 08/690,921, Aug. 1, 1996, abandoned, which is a continuation-in-part of application No. 08/649,811, May 17, 1996, abandoned, which is a continuation-in-part of application No. 08/562,346, Nov. 22, 1995, abandoned, which is a continuation-in-part of application No. 08/499,523, Jul. 7, 1995, Pat. No. 5,804,558, which is a continuation-in-part of application No. 08/451,832, filed as application No. PCT/US94/08305, Jul. 20, 1994, which is a continuation-in-part of application No. 08/243,879, May 17, 1994, Pat. No. 5,708,154, which is a continuation-in-part of application No. 08/182,483, Jan. 13, 1994, Pat. No. 5,693,486, which is a continuation-in-part of application No. 08/095,769, Jul. 26, 1993, Pat. No. 5,464,823, which is a continuation-in-part of application No. 08/093,926, Jul. 20, 1993, abandoned.

[51] Int. Cl.[7] .............................. A61K 7/16; A61K 9/68; C07K 7/08; C07K 7/02
[52] U.S. Cl. ............................... 514/2; 514/13; 424/49; 424/401; 424/413; 424/440; 530/324; 530/325; 530/326; 435/69.1; 435/252.3; 435/320.1
[58] Field of Search ........................ 514/12, 13; 424/49, 424/488

[56] References Cited

U.S. PATENT DOCUMENTS

| | | | |
|---|---|---|---|
| 4,323,694 | 4/1982 | Scala, Jr. .................. | 560/103 |
| 4,543,252 | 9/1985 | Lehrer et al. ............... | 514/12 |
| 4,652,639 | 3/1987 | Stabinsky ................... | 435/91.52 |
| 4,659,692 | 4/1987 | Lehrer et al. ............... | 514/12 |
| 4,705,777 | 11/1987 | Lehrer et al. ............... | 514/12 |
| 5,059,416 | 10/1991 | Cherukuri et al. .......... | 424/48 |
| 5,087,569 | 2/1992 | Gabay et al. ................ | 435/212 |
| 5,102,870 | 4/1992 | Florine et al. ............... | 514/12 |
| 5,126,257 | 6/1992 | Gabay et al. ................ | 435/212 |

(List continued on next page.)

FOREIGN PATENT DOCUMENTS

| | | |
|---|---|---|
| 272489 | 6/1988 | European Pat. Off. . |
| 545730 | 6/1993 | European Pat. Off. . |
| 89/11291 | 11/1989 | WIPO . |
| 93/01723 | 2/1993 | WIPO . |
| 93/19087 | 9/1993 | WIPO . |
| 93/24139 | 12/1993 | WIPO . |
| WO 94/02589 | 2/1994 | WIPO . |
| 94/21672 | 9/1994 | WIPO . |
| 95/03325 | 2/1995 | WIPO . |
| 95/10534 | 4/1995 | WIPO . |
| WO 95/26747 | 10/1995 | WIPO . |
| WO 96/04373 | 12/1996 | WIPO . |

OTHER PUBLICATIONS

Bateman et al., 1992, "The levels and biologic action of the human neutrophil granule peptide HP–1 in lung tumors," *Peptides* 13:133–139.

Bilgrami, S. et al., 1992, "Capnocytophage Bacteremia in Patient with Hodgkin's Disease following Bone Marrow Transplantion: Case Report and Review," *Clinical Infectious Diseases* 14:1045–1049.

(List continued on next page.)

*Primary Examiner*—Ponnathapu Achutamurthy
*Assistant Examiner*—William W. Moore
*Attorney, Agent, or Firm*—Pennie & Edmonds LLP

[57] ABSTRACT

The present invention provides methods and compositions suitable for treating oral mucositis in animals, including humans, with antimicrobial peptides such as protegrin peptides.

16 Claims, 7 Drawing Sheets

Change in Body Weight from Baseline

U.S. PATENT DOCUMENTS

| | | | |
|---|---|---|---|
| 5,171,739 | 12/1992 | Scott et al. | 514/12 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,338,724 | 8/1994 | Gabay et al. | 514/12 |
| 5,432,270 | 7/1995 | Zasloff et al. | 536/23.5 |
| 5,447,914 | 9/1995 | Travis et al. | 514/16 |
| 5,458,874 | 10/1995 | Pereira et al. | 424/85.1 |
| 5,459,235 | 10/1995 | Selsted et al. | 530/300 |
| 5,464,823 | 11/1995 | Lehrer et al. | 514/13 |
| 5,484,885 | 1/1996 | Pereira et al. | 530/326 |
| 5,486,503 | 1/1996 | Oppenheim et al. | 514/2 |
| 5,607,916 | 3/1997 | Pereira et al. | 514/12 |
| 5,614,545 | 3/1997 | Martin et al. | 514/398 |
| 5,631,228 | 5/1997 | Oppenheim et al. | 514/12 |
| 5,693,486 | 12/1997 | Lehrer et al. | 435/69.1 |
| 5,708,145 | 1/1998 | Lehrer et al. | 530/387.1 |

OTHER PUBLICATIONS

Broekaert et al., 1992, *Biochemistry* 31:4308–4314.

Cornelissen et al., 1993, *Plant Physiol.* 101:709–712.

Diamond et al., 1991, *Proc. Natl. Acad. Sci. U.S.A.* 88:3952–3956.

Donnelley, J.P. et al., 1993, "Failure of Clindamycin to Influence the Course of Severe Oromucositis Associated with Steptococcal Bactaeremia in Allogeneic Bone Marrow Transplant Recipients," *Scand. J. Infect. Dis.* 25:43–50.

Elsbach et al., 1993, *Current Opinion in Immunology* 5:103–107.

Haln et al., 1993, *Nature* 361:153–156.

Harwig et al., 1994, "Gallacins: cysteine–rich antimicrobial peptides of chicken leukocytes," *FEBS Lett.* 342:281–285.

Harwig et al., 1995, *J. Peptide Sci.* 3:207–215.

Harwig et al., 1995, *FEBS Lett.* 362:65–69.

Hoess et al., 1993, *EMBO Journal* 12:3351–3356.

Kokryakov et al., 1993, *FEBS Lett.* 327:231–236.

Lambert et al., 1989, *Proc. Natl. Acad. Sci. U.S.A.* 88:262–265.

Lehrer et al., 1985, *J. Virol.* 54:467–472.

Lehrer et al., 1991, *Cell* 64:229–230.

Lehrer et al., 1993, *Ann. Rev. Immunol.* 11:105–128.

Lerner, 1982, *Nature* 289:592–596.

Maloy & Kari, 1995, "Structure–activity studies on maganins and other host defense peptides," *Biopolymers (Peptide Science)* 37:105–122.

Masera et al., 1996, "Corticostatins/defensins inhibit in vitro NK activity and cytokine production by human peripheral blood mononuclear cells," *Regulatory Peptides* 62:13–21.

Masuda et al., 1992, "A novel anti–HIV synthetic peptide T–22 ([Tyr5, 12, Lys7]–polyphemusin II)," *Biochem. Biophys. Res. Commun.* 189:845–850.

Matsumoto et al., 1982, *Chem. and Pharma. Bulletin* 40(10):2701–2706.

Matsuzaki et al., 1991, "Interactions of an antimicrobial peptide, tachyplesin I, with lipid membranes," *Biochim. Biophys. Acta* 1070:259–264.

Matsuzaki et al., 1993, *Biochemistry* 32:11704–11710.

Mirgorodskaya et al., 1993, *FEBS Lett.* 330:339–342.

Miyata et al., 1989, *J. Biochem.* 106:663–668.

Morimoto et al., 1991, *Chemotherapy* 37:206–211.

Murakami et al., 1991, *Chemotherapy* 37:327–334.

Nakamura et al., 1988, *J. Biol. Chem.* 263:16709–16713.

Nakashima et al., 1992, *Antimicrobial Agents and Chemotherapy* pp. 1249–1255.

Olsson et al., 1991, *Biochim. Biophys. Acta.* 1097:37–44.

Park et al., 1992, "Conformation of tachyplesin I from Tachypleus tridentatus when interacting with lipid matrices," *Biochemistry* 31:12241–12247.

Pongor et al., 1987, *Methods in Enzymology* 154:450–473.

Robson et al., 1986, *Introduction to Proteins and Protein Engineering,* Elksevier, New York, p. 41.

Rustici et al., 1993, *Science* 259:361–364.

Schluesener et al., 1993, "Leukocyte antimicrobial peptides kill autoimmune T cells," *Journal of Neuroimmunology* 47:199–202.

Selsted et al., 1985, *J. Biol. Chem.* 260(8):4579–4584.

Selsted et al., 1992, "Enteric defensins: Antibiotic peptide components of intestinal host defense," *J. Celll Biol.* 118:929–936.

Selsted et al., 1993, *J. Biol. Chem.* 268:6641–6648.

Storici et al., 1993, *Biochem. Biophys. Res. Commun.* 196:1363–1368.

Tamamura et al., 1993, "Antimicrobial activity and conformation of tachyplesin I and its analogs," *Chemical and Pharmaceutical Bulletin* 41:978–980.

Tamamura et al., 1993, "A comparative study of the solution structure of tachyplesin I and a novel anti–HIV synthetic peptide, T22, determined by nuclear magnetic resonance," *Biochim. Biophys. Acta* 1163:209–216.

Tamamura et al., 1995, "Synthesis of protegrin–related peptides and their antibacterial and anti–Human Immunodeficiency Virus activity," *Chemical and Pharmaceutical Bulletin* 43:853–858.

Zhao et al., 1994, *FEBS Lett.* 346:285–288.

Zhao et al., 1995, *FEBS Lett.* 368:197–202.

Zhao et al., 1995, *FEBS Lett.* 376:130–134.

Harwig S. S. L. et al., 1996, "Intramolecular disulfide bonds enhance the antimicrobial and lytic activities of protegrins at physiological sodium chloride concentrations," *Eur. J. Biochem.* 240:352–357.

Yasin, B. et al., 1996, "Protegrins: Structural requirements for inactivating elementary bodies of Chlamydia trachomatis," *Infection and Immunity* 64(11):4863–4866.

Simmaco, M., et al., The Journal of Biological Chemistry, vol. 269, "Antimicrobial peptides from skin secretions of Rana esculenta", pp. 11956–11961, 1994.

Foote, R. L., et al., Journal of Clinical Oncology, vol. 12, "Randomized trial of a chlorhexidine mouthwash for alleviation of radiation–induced mucositis", pp. 2630–2633, 1994.

Epstein, J. B., et al., Oral Surgery, Oral Medicine and Oral Pathology, vol. 73, "Efficacy of chlorhexidine and nystatin rinses in prevention or oral complications in leukemia and bone marrow transplantation", pp. 682–689, 1992.

Donnelly, J. P., et al., Scandinavina Journal of Infectious Diseases, vol. 25, "Failure of clindamycin to influence the course of severe oromucositis associated wtih strptococcal bacteraemia in allogeneic bone marrow transplant recipients", pp. 43–50, 1993.

◯ = SIDE CHAIN
||||||| = HYDROGEN BOND

```
                            SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
         (A) LENGTH: 18 amino acids
         (B) TYPE: amino acid
         (C) STRANDEDNESS: unknown
         (D) TOPOLOGY: unknown (ii) MOLECULE TYPE: peptide (ix) FEATURE:
         (A) NAME/KEY: Other
         (B) LOCATION:
         (D) OTHER INFORMATION: C-terminal amidated (xi) SEQUENCE DESCRIPTION: SEQ ID NO:1:

Arg Gly Gly Arg Leu Cys Tyr Cys Arg Arg Arg Phe Cys Val Cys Val
 1               5                  10                  15

Gly Arg (2) INFORMATION FOR SEQ ID NO:2:

(i) SEQUENCE CHARACTERISTICS:
         (A) LENGTH: 18 amino acids
         (B) TYPE: amino acid
         (C) STRANDEDNESS: unknown
         (D) TOPOLOGY: unknown (ii) MOLECULE TYPE: peptide (ix) FEATURE:

(xi) SEQUENCE DESCRIPTION: SEQ ID NO:2:

Arg Gly Gly Arg Leu Cys Tyr Cys Arg Arg Arg Phe Cys Val Cys Val
 1               5                  10                  15

Gly Arg
```

(2) INFORMATION FOR SEQ ID NO:3:

(i) SEQUENCE CHARACTERISTICS:
        (A) LENGTH: 17 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:3:

```
Arg Gly Gly Leu Cys Tyr Cys Arg Gly Arg Phe Cys Val Cys Val Gly
 1               5                  10                  15
Arg
```

(2) INFORMATION FOR SEQ ID NO:4:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 10
        (D) OTHER INFORMATION: Xaa=MeGly
        (A) NAME/KEY: Other
        (B) LOCATION:
        (D) OTHER INFORMATION: C-terminal amidated (xi) SEQUENCE DESCRIPTION: SEQ ID NO:4:

```
Arg Leu Leu Arg Ala Cys Tyr Cys Arg Xaa Arg Phe Cys Val Cys Val
 1               5                  10                  15
Gly Arg
```

(2) INFORMATION FOR SEQ ID NO:5:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:5:

```
Arg Gly Gly Arg Leu Cys Tyr Cys Arg Pro Arg Phe Cys Val Cys Val
 1               5                  10                  15
Gly Arg
```

(2) INFORMATION FOR SEQ ID NO:6:

(i) SEQUENCE CHARACTERISTICS:
        (A) LENGTH: 18 amino acids
        (B) TYPE: amino acid (C) STRANDEDNESS: unknown
            (D) TOPOLOGY: unknown (ii) MOLECULE TYPE: peptide (ix) FEATURE:
            (A) NAME/KEY: Other
            (B) LOCATION:
            (D) OTHER INFORMATION: C-terminal amidated (xi) SEQUENCE DESCRIPTION: SEQ ID NO:6:

Arg Gly Gly Gly Leu Cys Tyr Lys Arg Gly Trp Ile Lys Phe Cys Val
 1               5                  10                  15

Gly Arg (2) INFORMATION FOR SEQ ID NO:7:

(i) SEQUENCE CHARACTERISTICS:
            (A) LENGTH: 17 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION:
            (D) OTHER INFORMATION: C-terminal amidated (xi) SEQUENCE DESCRIPTION: SEQ ID NO:7:

Arg Gly Trp Gly Leu Cys Tyr Cys Pro Arg Phe Cys Val Cys Val Gly
 1               5                  10                  15

Arg (2) INFORMATION FOR SEQ ID NO:8:

(i) SEQUENCE CHARACTERISTICS:
            (A) LENGTH: 15 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION:
            (D) OTHER INFORMATION: C-terminal amidated (xi) SEQUENCE DESCRIPTION: SEQ ID NO:8:

Arg Leu Cys Tyr Cys Arg Pro Arg Phe Cys Val Cys Val Gly Arg
 1               5                  10                  15

(2) INFORMATION FOR SEQ ID NO:9:

(i) SEQUENCE CHARACTERISTICS:
            (A) LENGTH: 18 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION:
            (D) OTHER INFORMATION: C-terminal amidated (xi) SEQUENCE DESCRIPTION: SEQ ID NO:9:

```
Arg Gly Gly Gly Leu Cys Tyr Thr Arg Pro Arg Phe Thr Val Cys Val
 1               5                  10                  15

Gly Arg
```

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:10:

```
Leu Cys Tyr Cys Arg Gly Arg Phe Cys Val Cys Val Gly Arg
 1               5                  10
```

(2) INFORMATION FOR SEQ ID NO:11:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:11:

```
Arg Trp Arg Leu Cys Tyr Cys Arg Pro Arg Phe Cys Val Cys Val
 1               5                  10                  15
```

(2) INFORMATION FOR SEQ ID NO:12:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:12:

```
Arg Gly Trp Arg Leu Cys Tyr Cys Arg Pro Arg Phe Cys Val Cys Val
 1               5                  10                  15

Gly Arg
```

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown

```
       (ii) MOLECULE TYPE: peptide (ix) FEATURE:
            (A) NAME/KEY: Other
            (B) LOCATION:
            (D) OTHER INFORMATION: C-terminal amidated (xi) SEQUENCE DESCRIPTION: SEQ ID NO:13:

Arg Gly Trp Arg Ala Cys Tyr Cys Arg Pro Arg Phe Cys Ala Cys Val
 1               5                  10                  15

Gly Arg (2) INFORMATION FOR SEQ ID NO:14:

(i) SEQUENCE CHARACTERISTICS:
            (A) LENGTH: 17 amino acids
            (B) TYPE: amino acid
            (C) STRANDEDNESS: single
            (D) TOPOLOGY: linear (ix) FEATURE:
            (A) NAME/KEY: Other
            (B) LOCATION:
            (D) OTHER INFORMATION: C-terminal amidated (xi) SEQUENCE DESCRIPTION: SEQ ID NO:14:

Gly Trp Arg Leu Cys Tyr Cys Arg Pro Arg Phe Cys Val Cys Val Gly
 1               5                  10                  15

Arg (2) INFORMATION FOR SEQ ID NO:15:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (ix) FEATURE:
            (A) NAME/KEY: Other
            (B) LOCATION: 1
            (D) OTHER INFORMATION: Xaa=Cha
            (A) NAME/KEY: Other
            (B) LOCATION:
            (D) OTHER INFORMATION: C-terminal amidated (xi) SEQUENCE DESCRIPTION: SEQ ID NO:15:

Xaa Cys Tyr Cys Arg Arg Arg Phe Cys Val Cys Val
 1               5                  10

(2) INFORMATION FOR SEQ ID NO:16:

(i) SEQUENCE CHARACTERISTICS:
            (A) LENGTH: 13 amino acids
            (B) TYPE: amino acid
            (C) STRANDEDNESS: unknown
            (D) TOPOLOGY: unknown (ii) MOLECULE TYPE: peptide (ix) FEATURE:

(xi) SEQUENCE DESCRIPTION: SEQ ID NO:16:

Trp Leu Cys Tyr Cys Arg Arg Arg Phe Cys Val Cys Val
 1               5                  10

(2) INFORMATION FOR SEQ ID NO:17:
```

```
      (i) SEQUENCE CHARACTERISTICS:
          (A) LENGTH: 13 amino acids
          (B) TYPE: amino acid
          (C) STRANDEDNESS: unknown
          (D) TOPOLOGY: unknown (ii) MOLECULE TYPE: peptide (ix) FEATURE:
          (A) NAME/KEY: Other
          (B) LOCATION: 7
          (D) OTHER INFORMATION: Xaa=MeGly
          (A) NAME/KEY: Other
          (B) LOCATION:
          (D) OTHER INFORMATION: C-terminal amidated (xi) SEQUENCE DESCRIPTION: SEQ ID NO:17:

Arg Leu Cys Tyr Cys Arg Xaa Arg Phe Cys Val Cys Val
 1               5                  10

(2) INFORMATION FOR SEQ ID NO:18:

(i) SEQUENCE CHARACTERISTICS:
          (A) LENGTH: 15 amino acids
          (B) TYPE: amino acid
          (C) STRANDEDNESS: unknown
          (D) TOPOLOGY: unknown (ii) MOLECULE TYPE: peptide (ix) FEATURE:

(xi) SEQUENCE DESCRIPTION: SEQ ID NO:18:

Arg Leu Cys Tyr Cys Arg Pro Arg Phe Cys Val Cys Val Gly Arg
 1               5                  10                  15

(2) INFORMATION FOR SEQ ID NO:19:

(i) SEQUENCE CHARACTERISTICS:
          (A) LENGTH: 18 amino acids
          (B) TYPE: amino acid
          (C) STRANDEDNESS: unknown
          (D) TOPOLOGY: unknown (ii) MOLECULE TYPE: peptide (ix) FEATURE:

(xi) SEQUENCE DESCRIPTION: SEQ ID NO:19:

Arg Gly Gly Gly Leu Cys Tyr Cys Arg Pro Arg Phe Cys Val Cys Val
 1               5                  10                  15

Gly Arg (2) INFORMATION FOR SEQ ID NO:20:

(i) SEQUENCE CHARACTERISTICS:
          (A) LENGTH: 13 amino acids
          (B) TYPE: amino acid
          (C) STRANDEDNESS: unknown
          (D) TOPOLOGY: unknown (ii) MOLECULE TYPE: peptide (ix) FEATURE:
          (A) NAME/KEY: Other
          (B) LOCATION: 2
          (D) OTHER INFORMATION: Xaa=Cha
          (A) NAME/KEY: Other
          (B) LOCATION:
          (D) OTHER INFORMATION: C-terminal amidated
```

(xi) SEQUENCE DESCRIPTION: SEQ ID NO:20:

Arg Xaa Cys Phe Cys Arg Pro Arg Phe Cys Val Cys Val
1               5                  10

(2) INFORMATION FOR SEQ ID NO:21:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:21:

Arg Trp Cys Phe Cys Arg Pro Arg Phe Cys Val Cys Val
1               5                  10

(2) INFORMATION FOR SEQ ID NO:22:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION: 3
        (D) OTHER INFORMATION: Xaa=Cha
        (A) NAME/KEY: Other
        (B) LOCATION: 8
        (D) OTHER INFORMATION: Xaa=Cha
        (A) NAME/KEY: Other
        (B) LOCATION:
        (D) OTHER INFORMATION: C-terminal amidated (xi) SEQUENCE DESCRIPTION: SEQ ID NO:22:

Leu Cys Xaa Cys Arg Arg Arg Xaa Cys Val Cys Val
1               5                  10

(2) INFORMATION FOR SEQ ID NO:23:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:23:

Arg Gly Gly Arg Leu Cys Tyr Cys Arg Arg Arg Phe Cys Val Cys
1               5                  10                  15

(2) INFORMATION FOR SEQ ID NO:24:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (ix) FEATURE:
              (A) NAME/KEY: Other
              (B) LOCATION:
              (D) OTHER INFORMATION: C-terminal amidated (xi) SEQUENCE DESCRIPTION: SEQ ID NO:24:

Leu Cys Tyr Thr Arg Arg Arg Phe Thr Val Cys Val
1               5                   10

(2) INFORMATION FOR SEQ ID NO:25:

(i) SEQUENCE CHARACTERISTICS:
              (A) LENGTH: 15 amino acids
              (B) TYPE: amino acid
              (C) STRANDEDNESS: unknown
              (D) TOPOLOGY: unknown (ii) MOLECULE TYPE: peptide (ix) FEATURE:
              (A) NAME/KEY: Other
              (B) LOCATION:
              (D) OTHER INFORMATION: C-terminal amidated (xi) SEQUENCE DESCRIPTION: SEQ ID NO:25:

Arg Arg Cys Tyr Cys Arg Arg Arg Phe Cys Val Cys Val Gly Arg
1               5                   10                  15

(2) INFORMATION FOR SEQ ID NO:26:

(i) SEQUENCE CHARACTERISTICS:
              (A) LENGTH: 13 amino acids
              (B) TYPE: amino acid
              (C) STRANDEDNESS: unknown
              (D) TOPOLOGY: unknown (ii) MOLECULE TYPE: peptide (ix) FEATURE:

(xi) SEQUENCE DESCRIPTION: SEQ ID NO:26:

Arg Leu Cys Tyr Cys Arg Arg Phe Cys Val Cys Val
1               5                   10

(2) INFORMATION FOR SEQ ID NO:27:

(i) SEQUENCE CHARACTERISTICS:
              (A) LENGTH: 15 amino acids
              (B) TYPE: amino acid
              (C) STRANDEDNESS: unknown
              (D) TOPOLOGY: unknown (ii) MOLECULE TYPE: peptide (ix) FEATURE:
              (A) NAME/KEY: Other
              (B) LOCATION: 2
              (D) OTHER INFORMATION: Xaa=Cha
              (A) NAME/KEY: Other
              (B) LOCATION: 9
              (D) OTHER INFORMATION: Xaa=MeGly
              (A) NAME/KEY: Other
              (B) LOCATION:
              (D) OTHER INFORMATION: C-terminal amidated (xi) SEQUENCE DESCRIPTION: SEQ ID NO:27:

Arg Xaa Arg Leu Cys Tyr Cys Arg Xaa Arg Phe Cys Val Cys Val
1               5                   10                  15

(2) INFORMATION FOR SEQ ID NO:28:

```
    (i) SEQUENCE CHARACTERISTICS:
         (A) LENGTH: 16 amino acids
         (B) TYPE: amino acid
         (C) STRANDEDNESS: unknown
         (D) TOPOLOGY: unknown (ii) MOLECULE TYPE: peptide (ix) FEATURE:
         (A) NAME/KEY: Other
         (B) LOCATION: 12
         (D) OTHER INFORMATION: Xaa=Cha
         (A) NAME/KEY: Other
         (B) LOCATION:
         (D) OTHER INFORMATION: C-terminal amidated (xi) SEQUENCE DESCRIPTION: SEQ ID NO:28:

Arg Gly Trp Arg Leu Cys Tyr Cys Arg Gly Arg Xaa Cys Val Cys Val
 1               5                  10                  15

(2) INFORMATION FOR SEQ ID NO:29:

(i) SEQUENCE CHARACTERISTICS:
         (A) LENGTH: 18 amino acids
         (B) TYPE: amino acid
         (C) STRANDEDNESS: unknown
         (D) TOPOLOGY: unknown (ii) MOLECULE TYPE: peptide (ix) FEATURE:
         (A) NAME/KEY: Other
         (B) LOCATION: 5
         (D) OTHER INFORMATION: Xaa=Cha
         (A) NAME/KEY: Other
         (B) LOCATION:
         (D) OTHER INFORMATION: C-terminal amidated (xi) SEQUENCE DESCRIPTION: SEQ ID NO:29:

Arg Gly Leu Arg Xaa Cys Tyr Cys Arg Gly Arg Phe Cys Val Cys Val
 1               5                  10                  15

Gly Arg (2) INFORMATION FOR SEQ ID NO:30:

(i) SEQUENCE CHARACTERISTICS:
         (A) LENGTH: 18 amino acids
         (B) TYPE: amino acid
         (C) STRANDEDNESS: unknown
         (D) TOPOLOGY: unknown (ii) MOLECULE TYPE: peptide (ix) FEATURE:
         (A) NAME/KEY: Other
         (B) LOCATION:
         (D) OTHER INFORMATION: C-terminal amidated (xi) SEQUENCE DESCRIPTION: SEQ ID NO:30:

Arg Gly Trp Arg Gly Cys Tyr Lys Arg Gly Arg Phe Lys Gly Cys Val
 1               5                  10                  15

Gly Arg (2) INFORMATION FOR SEQ ID NO:31:

(i) SEQUENCE CHARACTERISTICS:
         (A) LENGTH: 15 amino acids
         (B) TYPE: amino acid
         (C) STRANDEDNESS: unknown
         (D) TOPOLOGY: unknown
```

```
        (ii) MOLECULE TYPE: peptide (ix) FEATURE:
              (A) NAME/KEY: Other
              (B) LOCATION: 10
              (D) OTHER INFORMATION: Xaa= MeGly
              (A) NAME/KEY: Other
              (B) LOCATION:
              (D) OTHER INFORMATION: C-terminal amidated (xi) SEQUENCE DESCRIPTION: SEQ ID NO:31:

Arg Gly Trp Arg Gly Cys Tyr Cys Arg Xaa Arg Phe Cys Gly Cys
1               5                   10                  15

(2) INFORMATION FOR SEQ ID NO:32:

(i) SEQUENCE CHARACTERISTICS:
              (A) LENGTH: 17 amino acids
              (B) TYPE: amino acid
              (C) STRANDEDNESS: unknown
              (D) TOPOLOGY: unknown (ii) MOLECULE TYPE: peptide (ix) FEATURE:
              (A) NAME/KEY: Other
              (B) LOCATION:
              (D) OTHER INFORMATION: C-terminal amidated (xi) SEQUENCE DESCRIPTION: SEQ ID NO:32:

Arg Gly Gly Leu Cys Tyr Cys Arg Gly Arg Phe Cys Val Cys Val Gly
1               5                   10                  15

Arg (2) INFORMATION FOR SEQ ID NO:33:

(i) SEQUENCE CHARACTERISTICS:
              (A) LENGTH: 18 amino acids
              (B) TYPE: amino acid
              (C) STRANDEDNESS: unknown
              (D) TOPOLOGY: unknown (ii) MOLECULE TYPE: peptide (ix) FEATURE:
              (A) NAME/KEY: Other
              (B) LOCATION: 10
              (D) OTHER INFORMATION: Xaa=MeGly
              (A) NAME/KEY: Other
              (B) LOCATION:
              (D) OTHER INFORMATION: C-terminal amidated (xi) SEQUENCE DESCRIPTION: SEQ ID NO:33:

Arg Leu Leu Arg Leu Cys Tyr Cys Arg Xaa Arg Phe Cys Val Cys Val
1               5                   10                  15

Gly Arg (2) INFORMATION FOR SEQ ID NO:34:

(i) SEQUENCE CHARACTERISTICS:
              (A) LENGTH: 18 amino acids
              (B) TYPE: amino acid
              (C) STRANDEDNESS: unknown
              (D) TOPOLOGY: unknown (ii) MOLECULE TYPE: peptide (ix) FEATURE:

(xi) SEQUENCE DESCRIPTION: SEQ ID NO:34:
```

Arg Gly Gly Arg Leu Cys Tyr Cys Arg Gly Arg Phe Cys Val Cys Val
1               5                   10                  15

Gly Arg (2) INFORMATION FOR SEQ ID NO:35:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:35:

Arg Gly Trp Arg Leu Cys Tyr Cys Arg Gly Arg Phe Cys Val Cys Val
1               5                   10                  15

Gly Arg (2) INFORMATION FOR SEQ ID NO:36:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:36:

Arg Gly Gly Arg Leu Cys Tyr Cys Arg Gly Arg Phe Cys Val Cys Val
1               5                   10                  15

Gly Arg (2) INFORMATION FOR SEQ ID NO:37:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:37:

Arg Gly Gly Arg Val Cys Tyr Cys Arg Gly Arg Phe Cys Val Cys Val
1               5                   10                  15

Gly Arg (2) INFORMATION FOR SEQ ID NO:38:

(i) SEQUENCE CHARACTERISTICS:

(A) LENGTH: 16 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:38:

Arg Gly Gly Arg Val Cys Tyr Cys Arg Gly Arg Phe Cys Val Cys Val
 1               5                  10                  15

(2) INFORMATION FOR SEQ ID NO:39:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (ix) FEATURE:

(xi) SEQUENCE DESCRIPTION: SEQ ID NO:39:

Arg Gly Gly Arg Val Cys Tyr Cys Arg Gly Arg Phe Cys Val Cys Val
 1               5                  10                  15

(2) INFORMATION FOR SEQ ID NO:40:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:40:

Trp Leu Cys Tyr Cys Arg Arg Arg Phe Cys Val Cys Val
 1               5                  10

(2) INFORMATION FOR SEQ ID NO:41:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:41:

Arg Gly Gly Gly Leu Cys Tyr Ala Arg Gly Trp Ile Ala Phe Cys Val
 1               5                  10                  15
Cys Val Gly Arg
            20

(2) INFORMATION FOR SEQ ID NO:42:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:42:

Leu Cys Tyr Cys Arg Arg Arg Phe Cys Val Cys Val Phe
1               5                   10

(2) INFORMATION FOR SEQ ID NO:43:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:43:

Arg Leu Cys Tyr Cys Arg Pro Arg Phe Cys Val Cys Val
1               5                   10

(2) INFORMATION FOR SEQ ID NO:44:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:44:

Arg Leu Cys Ala Cys Arg Gly Arg Ala Cys Val Cys Val
1               5                   10

(2) INFORMATION FOR SEQ ID NO:45:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:45:

Arg Gly Gly Arg Leu Cys Tyr Cys Arg Arg Arg Phe Cys Ile Cys Val
 1               5                   10                  15

(2) INFORMATION FOR SEQ ID NO:46:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:46:

Arg Gly Gly Gly Leu Cys Tyr Cys Arg Arg Arg Phe Cys Val Cys Val
 1               5                   10                  15

Gly Arg (2) INFORMATION FOR SEQ ID NO:47:

(i) SEQUENCE CHARACTERISTICS:
        (A) LENGTH: 18 amino acids
        (B) TYPE: amino acid
        (C) STRANDEDNESS: unknown
        (D) TOPOLOGY: unknown (ii) MOLECULE TYPE: peptide (ix) FEATURE:
        (A) NAME/KEY: Other
        (B) LOCATION:
        (D) OTHER INFORMATION: C-terminal amidated (xi) SEQUENCE DESCRIPTION: SEQ ID NO:47:

Arg Gly Gly Arg Leu Cys Tyr Cys Arg Gly Trp Ile Cys Phe Cys Val
 1               5                   10                  15

Gly Arg

COMPOSITIONS AND METHODS FOR THE PREVENTION AND TREATMENT OF ORAL MUCOSITIS

CROSS-REFERENCE TO RELATED APPLICATIONS

This application is a continuation-in-part of U.S. Ser. No. 08/690,921, now abandoned, filed Aug. 1, 1996, which is a continuation-in-part of U.S. Ser. No. 08/649,811 filed May 17, 1996, now abandoned which is a continuation-in-part of U.S. Ser. No. 08/562,346 filed Nov. 22, 1995, now abandoned which is a continuation-in-part of U.S. Ser. No. 08/499,523 filed Jul. 7, 1995, now U.S. Pat. No. 5,804,558, which is a continuation-in-part of U.S. Ser. No. 08/451,832 filed May 26, 1995, now abandoned which claims priority from PCT/US94/08305 (WO 95/03325) filed Jul. 20, 1994 and which is a continuation-in-part of U.S. Ser. No. 08/243,879 filed May 17, 1994, now U.S. Pat. No. 5,708,154 which is a continuation-in-part of U.S. Ser. No. 08/182,483 filed Jan. 13, 1994, now U.S. Pat. No. 5,693,486 which is a continuation-in-part of U.S. Ser. No. 08/095,769 filed Jul. 26, 1993, now U.S. Pat. No. 5,464,823 which is a continuation-in-part of U.S. Ser. No. 08/093,926 filed Jul. 20, 1993, now abandoned. Benefit is claimed under 35 U.S.C. § 120 with respect to U.S. Ser. Nos. 08/960,921, 08/649,811 and 08/562,346. The contents of these applications are incorporated herein by reference in their entireties.

FIELD OF THE INVENTION

The present invention relates to the use of antimicrobial peptides to treat or prevent oral mucositis. In particular, the present invention relates to the use of protegrin peptides and congeners thereof to treat oral mucositis in animals including humans.

BACKGROUND OF THE INVENTION

Oral mucositis is a significant side effect of cancer therapy and bone marrow transplantation that is not adequately managed by current approaches (Sonis, 1993a, "Oral Complications," In: *Cancer Medicine*, pp. 2381–2388, Holland et al., Eds., Lea and Febiger, Philadelphia; Sonis, 1993b, "Oral Complications in Cancer Therapy," In: *Principles and Practice of Oncology*, pp. 2385–2394, DeVitta et al., Eds., J. B. Lippincott, Philadelphia). Oral mucositis is found in almost 100% of patients receiving chemotherapy and radiotherapy for head and neck tumors and in about 90% of children with leukemia. About 40% of patients treated with chemotherapy for other tumors develop oral problems during each exposure to the chemotherapeutic agent (Sonis, 1993b, supra). Additionally, approximately 75% of patients undergoing bone marrow transplantation, both autologous and allogeneic, develop mucositis (Woo et al., 1993, *Cancer* 72:1612–1617). Current estimates indicate that about 400,000 patients suffer from oral mucositis annually in the United States alone (Graham et al., 1993, *Cancer Nursing* 16:117–122). Given that patients often receive multiple cycles of chemo- and/or radiotherapy, there are an estimated 1,000,000 incidences of oral mucositis per year in the United States.

The incidence of oral mucositis varies depending on the type of tumor, age of the patient, and state of oral health. The therapies used in these different tumors are an important factor with the very aggressive chemotherapy protocols used in bone marrow transplant being associated with a high incidence of oral mucositis. Younger patients have a higher incidence, which may be due to their more rapid epithelial cell turnover, and hence susceptibility to cytotoxic drugs (Sonis 1993a, supra).

Incidence is also related to the choice of chemotherapeutic agent, with agents such as carmustine (BCNU), chlorambucil (Leukeran), cisplatin (Platinol), Cytarabine, doxorubicin (Adriamycin), fluorouracil (5-FU), methoxetrate (Mexate) and plicamycin (Mithracin) being known for their direct stomatotoxic potential (Sonis, 1993b, supra) and hence incidence of oral mucositis. The increasing use of aggressive infusion protocols is also associated with an increased incidence of oral mucositis.

Oral mucositis is initiated by the cytotoxic effects of chemotherapy and/or radiotherapy on the rapidly dividing epithelial cells of the oropharyngeal mucosa, and is exacerbated by infection with both endogenous oral flora and opportunistic bacterial and fungal pathogens. Complications related to oral mucositis vary in the different patient populations affected, but include pain, poor oral intake with consequent dehydration and weight loss, and systemic infection with organisms originating in the oral cavity (Sonis, 1993b, supra). The pain associated with oral mucositis may be severe requiring narcotic analgesics, and the difficulty in eating can result in patients receiving total parenteral nutrition. The damaged oral epithelium and defective immune response often found in these patients offers a ready route for entry of organisms from the mouth into the systemic circulation. This is a major concern due to the potential for sepsis, and injectable antibiotics are used when signs of systemic infection are observed. Due to these complications, oral mucositis can be a dose-limiting toxicity of radiation or chemotherapy treatment, resulting in inadequate therapy for the cancer.

A variety of approaches to the treatment of oral mucositis and associated oral infections have been tested with limited success. For example, the use of an allopurinol mouthwash, an oral sucralfate slurry, and pentoxifylline were reported in preliminary studies to result in a decrease in mucositis. Subsequent randomized and controlled studies, however, have failed to demonstrate any benefit to treatment with these agents (Loprinzi et al., 1995, *Sem. Oncol.* 22 *Supple.* 3):95–97; Epstein & Wong, 1994, *Int. J. Radiation Oncology Biol. Phys.* 28:693–698; Verdi et al., 1995, *Oral Surg. Oral Med. Oral Pathol. Oral Radiol. Endod.* 80:36–42).

Other therapies have been directed at decreasing oral flora and the extent of infection of oral ulcerations. Systemic treatment with G- and GM-CSF has been shown to result in a decreased incidence of oral mucositis, presumably by allowing for more rapid neutrophil recovery and thus an improved ability to combat infection, although it has been postulated that the CSFs may have a more direct effect on the oral mucosa (Chi et al., 1995, *J. Clin. Oncol.* 13:2620–2628). In one study, GM-CSF was reported to exacerbate mucositis. (Cartee et al., 1994, *Cytokine* 7:471–477). Benzydamine hydrochloride, a nonsteroidal drug with analgesic and antimicrobial properties, has been studied both in patients undergoing radiation therapy and in patients receiving intra-arterial chemotherapy (Epstein et al., 1986, *Oral Surg. Oral Med. Oral Pathol.* 62:145–148; Epstein et al., 1989, *Int. J. Radiation Oncology Biol. Phys.* 16:1571–1575).

Chlorhexidine, an antimicrobial mouth rinse, has also been used extensively in the treatment and prevention of oral mucositis (Ferretti et al., 1990, *Bone Marrow Transplan.* 3:483–493; Weisdorf et al., 1989, *Bone Marrow Transplan.* 4:89–95). It has been noted however that the efficacy of chlorhexidine is significantly decreased in saliva, and that this compound is relatively ineffective against the Gram negative bacteria that tend to colonize the oral cavity in patients undergoing radiation therapy (Spijkervet et al., 1990, *Oral Surg. Oral Med. Oral Pathol.* 69:444–449). In addition, at least one study has shown that the use of chlorhexidine may be detrimental and result in a higher incidence of mucositis (Foote et al., 1994, *J. Clin Oncol.* 12:2630–2633).

Several studies have shown that the use of a vancomycin paste and antibiotic lozenges containing polymixin B, tobramycin and amphotericin B in patients undergoing myelosuppresive chemotherapy or radiation therapy can result in a decrease in oral mucositis and in the incidence of sepsis due to alpha hemolytic streptococci (Barker et al., 1995, *J. Ped. Hem. Oncol.* 17:151–155; Spijkervet et al., 1991, In: *Irradiation Mucositis*, Munksgaard Press, pp. 43–50). Despite the clear need for therapeutic agents to treat oral mucositis, no drugs are currently approved for this indication. As a result, there is no standard treatment for this disorder.

Topical application of agents useful to treat oral diseases such as oral mucositis presents unique problems. For example, due to salivation and/or food or fluid intake, it is oftentimes extremely difficult to attain sufficient mucoadhesion and residence time in the mouth for the agent to be effective. Topical application of peptides is even more problematic, as the peptides must be stable to proteolytic enzymes resident in saliva. Other difficulties associated with topical oral application of drugs include tooth discoloration and patient compliance. Oral formulations providing good mucoadhesion and residence time in the mouth while at the same time providing high levels of patient compliance are not readily available.

Hence, the availability of compositions and methods for treating oral mucositis which exhibit broad spectrum antimicrobial activity, good stability, mucoadhesion and residence time in the mouth and which yield high levels of patient compliance are extremely desirable, and are therefore objects of the present invention.

SUMMARY OF THE INVENTION

These and other objects are provided by the present invention, which in one aspect relates to methods of treating and/or preventing oral mucositis with antimicrobial peptides. The methods generally involve administering to an animal in need thereof an amount of an antimicrobial peptide effective to treat or prevent oral mucositis. Generally, antimicrobial peptides useful in the methods of the invention are protegrin peptides and/or congeners thereof. However, other broad spectrum antimicrobial peptides such as magainins, dermaseptins, PGLa or XPF peptides, adrenoregulins, BPI protein and peptides, caeruleins, performs, insect defensins or sapecins, rabbit or human cationic antimicrobial peptides (CAP-18), porcine myeloid antibacterial peptides (PMAP), aibellins, acerins, brevenins, esculentins, lactoferrins, cecropin-mellitin hybrids (CEMA peptides), bombenins, tachyplesins, polyphemusins and defensins may be used as well.

In one illustrative embodiment of the invention, protegrin peptides useful for the treatment or prophylaxis of oral mucositis are peptides having the formula:

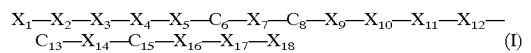

(I)

or pharmaceutical salts thereof, wherein: each of $C_8$ and $C_{13}$ is independently present or not present, and if present each is independently a cysteine-like, basic, small, polar/large or hydrophobic;

each of $C_6$ and $C_{15}$ is independently a cysteine-like, basic, small, polar/large or hydrophobic amino acid;

each of $X_1$–$X_5$ is independently present or not present, and if present each is independently a basic, hydrophobic, polar/large, or small amino acid;

each of $X_7$ and $X_{14}$ is independently a hydrophobic or a small amino acid;

each of $X_9$ and $X_{12}$ is independently present or not present;

$X_9$–$X_{12}$ taken together are capable of effecting a reverse-turn when contained in the amino acid sequence of formula (I) and at least one of $X_9$–$X_{12}$ must be a basic amino acid;

each of $X_{16}$–$X_{18}$ is independently present or not present, and if present each is independently a basic, hydrophobic, polar/large or small amino acid;

and wherein at least about 15% up to about 50% of the amino acids comprising said antimicrobial peptide are basic amino acids such that said antimicrobial peptide has a net charge of at least +1 at physiological pH.

Also contemplated for use in the methods of the invention are the N-terminal acylated and/or C-terminal amidated or esterified forms of the peptides of formula (I), as well as linear or disulfide-bridged forms.

In another aspect, the present invention is directed to a pharmaceutical formulation suited to topical application of antimicrobial agents to the oral cavity of animals, including humans. The pharmaceutical formulation of the invention generally comprises an antimicrobial compound in admixture with a gel-like vehicle. The gel-like vehicle generally comprises a mixture of a water-soluble gelling agent and a humectant, and may optionally contain other ingredients such as sweetening agents, preservatives, etc. The gel-like formulation provides superior mucoadhesion properties and residence time in the mouth, and has favorable moistening and flavor properties associated with high patient compliance. The gel-like formulation is particularly suited for use with the methods described herein.

DETAILED DESCRIPTION OF THE INVENTION

Figure 1:
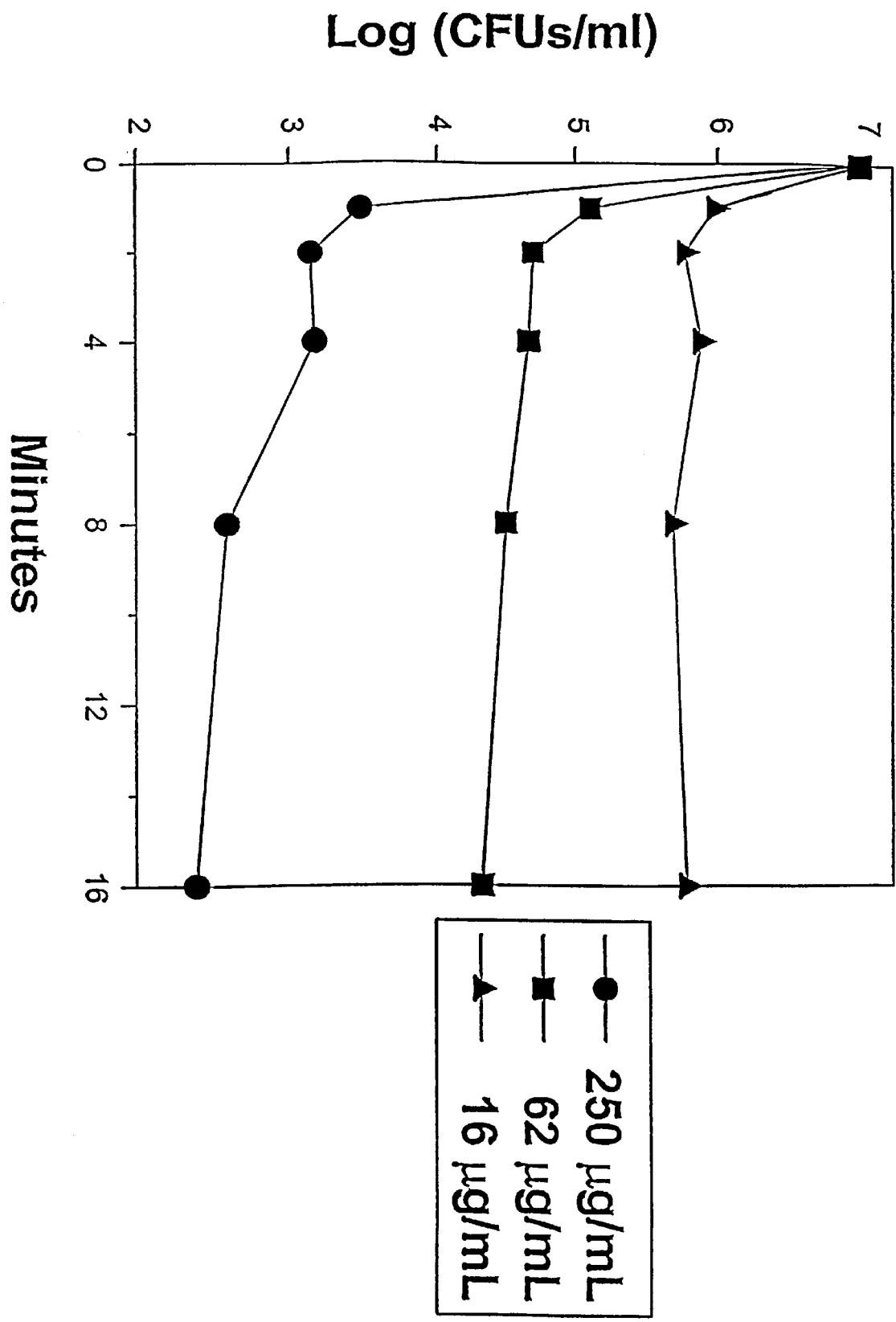
FIG. 1 is a graphical representation of the effect of peptide OM-3 (SEQ ID NO:3) on colony forming units ("CFUs") of microflora in pooled normal human saliva.

The present invention relates to compositions and methods for the treatment or prevention of oral mucositis in animals, including humans. As discussed in the Summary of the Invention, oral mucositis develops in a significant number of cancer and bone marrow transplantation patients receiving chemotherapy and/or radiotherapy.

Complications related to oral mucositis vary in the different patient populations affected, but include pain, poor oral intake with consequent dehydration and weight loss, and systemic infection with organisms originating in the oral cavity (Sonis, 1993b). The pain associated with oral mucositis may be severe, requiring narcotic analgesics, and the difficulty in eating can result in patients receiving total parenteral nutrition. The damaged oral epithelium and defective immune response often found in these patients offers a ready route for entry of organisms from the mouth into the systemic circulation. This is a major concern due to the potential for sepsis, and injectable antibiotics are used when signs of systemic infection are observed. Due to these complications, oral mucositis can be a dose-limiting toxicity of radiation or chemotherapy treatment resulting in inadequate therapy for the cancer.

The oral cavity is colonized by a variety of organisms including alpha and non-hemolytic streptococci, group D streptococci, Corynebacterium species, staphylococci, lactobacilli, Neisseria species, Branhamella catarrhalis, Hemophilus parainfluenzae, Hemophilus influenzae, Acinetobacter species, Mycoplasma species, and spirochetes. Anaerobic organisms have been detected as well. Important potential pathogens such as S. pneumoniae, Klebsiella pneumoniae, P. aeruginosa, N. meningitidis, and Proteus mirabilis have also been identified in normal oral flora (Loesche, 1994, "Ecology of the Oral Flora," In: Oral Microbiology and Immunology, R. J. Nisengard and M. G. Newman, Eds., W. B. Saunders Co., Philadelphia, pp. 307–315). Cancer patients have been observed to have increased numbers of organisms in the oral cavity, most likely because of poor dental hygiene and xerostomia. These patients have also been shown to have a shift in the oral flora from predominantly Gram positive organisms to predominantly Gram negative organisms (Sonis, 1993, "Oral Complications," In: Cancer Medicine, 3rd Edition, J. L. Holland et al., Eds., Lea and Febiger, Philadelphia, pp. 2381–2388; Spijkervet et al., 1991, "Effect of Selective Elimination of the Oral Flora on Mucositis in Irradiated Head and Neck Cancer Patients," J. Surg. Oncol. 46:167–173). All of these organisms, as well as viruses and fungi, may be involved in oral mucositis.

Thus, agents useful to treat oral mucositis must exhibit broad spectrum antimicrobial activity, particularly against Gram-negative microorganisms (Sonis, 1993, "Oral Complications of Cancer Therapy," In: Principles and Practice of Oncology, V. DeVitta et al., Eds., J. B. Lippincott, Philadelphia). Additional advantageous properties of agents useful to treat oral mucositis include fast kill kinetics and low frequency of microbial resistance.

Protegrin peptides are a recognized class of naturally occurring antimicrobial peptides that exhibit broad spectrum antimicrobial activity against Gram-positive and Gram-negative bacteria, yeast, fungi and certain viruses (for a review of the properties of protegrin peptides see, U.S. Pat. No. 5,464,823 and WO 95/03325 and references cited therein). To date, five different naturally occurring protegrin peptides have been identified, designated PG-1 through PG-5, having the following amino acid sequences:

(PG-1) RGGRLCYCRRRFCVCVGR (SEQ ID NO:1)
(PG-2) RGGRLCYCRRRFCICV (SEQ ID NO:45)
(PG-3) RGGGLCYCRRRFCVCVGR (SEQ ID NO:46)
(PG-4) RGGRLCYCRGWICFCVGR (SEQ ID NO:47)
(PG-5) RGGRLCYCRDRFCVCVGR (SEQ ID NO:5)

Protegrins PG-1 through PG-5 are amidated at the C-terminus and have two disulfide linkages; one between $C_6$ and $C_1$ and another between $C_8$ and $C_{13}$.

Recently, a number of congeners of protegrin peptides have been designed (see U.S. Ser. Nos. 08/451,832, 08/499,523, 08/562,346, 08/649,811 and 08/960,921). These protegrins, like the naturally occurring protegrins, exhibit broad spectrum antimicrobial activity.

Quite unexpectedly, it has been discovered that antimicrobial peptides such as the protegrin peptides are capable of exhibiting broad spectrum antimicrobial activity against the normal oral flora of animals, as well as against opportunistic pathogens associated with oral mucositis. Importantly, this antimicrobial activity is effected within the natural environment of the oral cavity, particularly in saliva. Additionally, it was unexpectedly discovered that treatment with protegrins prevents the onset of mucositis. Based on these surprising discoveries, it was surmised that such peptides would be effective to treat or prevent oral infections such as oral mucositis.

Treatment of oral mucositis with protegrins, especially with the compositions of the invention, provides myriad advantages over other treatments. The protegrins exhibit antimicrobial activity against pathogens and opportunistic infections associated with mucositis, particularly against the Gram-negative bacteria observed in cancer patients. Unlike vancomycin and other antibiotics, protegrins kill oral pathogens in minutes rather than hours, making them ideally suited for topical application in the mouth where it is difficult to achieve the long residence times necessary for other treatments to be effective. And unlike traditional antibiotics such as vancomycin, protegrins exhibit a low frequency of resistance, making them ideally suited for treating infections such as oral mucositis.

The formulations of the invention provide myriad advantages as well. The compositions provide superior mucoadhesion, permitting the active ingredient to remain in contact with the mucosa for long durations. Additionally, through the use of a humectant, the formulations act to moisten the oral mucosa, leading to higher patient compliance. The humectant also acts as a water barrier, preventing the treatment from being washed away by saliva or other fluids. The vehicle also has a pleasant flavor, an important factor in achieving high patient compliance.

The Compounds

Antimicrobial peptides useful for treating or preventing oral mucositis according to the invention include virtually any broad spectrum antimicrobial peptides that exhibit efficacy against the pathogens associated with oral mucositis in the oral environment of the subject being treated. Such antimicrobial peptides include, but are not limited to, cationic amphipathic peptides such as dermaseptins or derivatives or analogues thereof (Mor et al., 1991, Biochemistry 30:8824; Mor et al., 1991, Biochemistry 33:6642; Mor et al., 1994, Eur. J. Biochem. 219:145); magainin peptides or derivatives or analogues thereof (Zasloff, 1987, Proc. Natl. Acad. Sci. U.S.A. 84:5449); PGLa or XPF peptides or derivatives or analogues thereof (Hoffman et al., 1983, EMBO J. 2:711; Andreu et al., 1985, Biochem. J. 149:531; Gibson et al., 1986, J. Biol. Chem. 261:5341; Giovannini et al., 1987, Biochem. J. 243:113); CPF peptides (Richter et al., 1986, J. Biol. Chem. 261:3676; U.S. Pat. No. 5,073,542)); adrenoregulins or derivatives or analogues thereof (Donly et al., 1992, Proc. Natl. Acad. Sci. U.S.A. 89:10960; Amiche et al., 1993, *Biochem. Biophys. Res. Commun.* 191:983); performs or derivatives or analogues thereof (Henkart et al., 1984, *J. Exp. Med.* 160:695); caerulein or derivatives or analogues thereof (Richter et al., 1988, *J. Biol. Chem.* 261:3676–3680; and Gibson et al., 1986, *J. Biol. Chem.* 261:5341–5349); Bacterial/Permeability-Increasing Protein (BPI) or peptide derivatives or analogues thereof (Ooi et al., 1987, *J. Biol. Chem.* 262:14891–14898; Qi et al., 1994, *Biochem. J.* 298:771–718; Gray and Haseman, 1994, *Infection and Immunity* 62:2732–2739; Little et al., 1994, *J. Biol. Chem.* 269:1865–1872; and U.S. Pat. No. 5,348,942); insect defensins (also called sapecins) or analogues or derivatives thereof (Alvarez-Bravo et al., 1994, *Biochem. J.* 302:535–538; Yamada and Natori, 1994, *Biochem. J.* 298:623–628; Kum et al., 1994, *FEBS Letters* 342:189–192; Shimoda et al., 1994, *FEBS Letters* 339:59–62; Yamada and Natori, 1993, *Biochem. J.* 291:275–279; Homma et al., 1992, *Biochem. J.* 288:281–284; Hanzawa et al., 1990, *FEBS Letters* 269:413–420; Kuzuhara et al., 1990, *Biochem. J.* 107:514–518; Matsuyama and Natori, 1990, *Biochem. J.* 108:128–132; U.S. Pat. No. 5,107,486; European Patent No. 303,859; European Patent No. 280,859; U.S. Pat. No. 5,008,371; U.S. Pat. No. 5,106,735; and U.S. Pat. No. 5,118,789); rabbit or human FALL-39/CAP-18 (Cationic Antimicrobial Protein) or analogues or derivatives thereof (PCT Application WO 94/02589 and references cited therein; Agerberth et al., 1995, *Proc. Natl. Acad. Sci. U.S.A.* 92:195–199; Larrick et al., 1991, *Biochem. Biophys. Res. Commun.* 179:170–175; Hirata et al., 1990, Endotoxin: Advances in Experimental Medicine and Biology (Herman Friedman, T. W. Klein, Masayasu Nakano, and Alois Nowotny, eds.); Tossi et al., 1994, *FEBS Letters* 339:108–112; Larrick et al., 1994, *J. Immunol.* 152:231–240; Hirata et al., 1994, *Infection and Immunity* 62:1421–1426; and Larrick et al., 1993, *Antimicrobial Agents and Chemotherapy* 37:2534–2539; PMAP (Porcine Myeloid Antibacterial Peptide) or analogues or derivatives thereof (Zanetti et al., 1994, *J. Biol. Chem.* 269:7855–7858; Storici et al., 1994, *FEBS Letters* 37:303–307; and Tossi et al., 1995, *Eur. J. Biochem.* 228:941–948); aibellin or analogues or derivatives thereof (Hino et al., 1994, *J. Dairy Sci.* 77:3426–3461; Kumazawa et al., 1994, *J. Antibiot.* 47:1136–1144; and Hino et al., 1993, *J. Dairy Sci.* 76:2213–2221); caerin or analogues or derivatives thereof (Stone et al., 1992, *J. Chem. Soc. Perkin Trans.* 1:3173–3178; and PCT WO 92/13881, published Aug. 20, 1992); bombinin or analogues or derivatives thereof (Simmaco et al., 1991, *Eur. J. Biochem.* 199:217–222 and Gibson et al., 1991, *J. Biol. Chem.* 266:23103–23111); brevenin or analogues or derivatives thereof (Morikawa et al., 1992, *Biochem. Biophys. Res. Commun.* 189:184–190; and Japanese Patent Application No. 6,080,695A); esculetin or analogues or derivatives thereof (Simmaco et al., 1993, *FEBS letters* 324:159–161; and Simmaco et al., 1994, *J. Biol. Chem.* 269:11956–11961); lactoferrin or analogues or derivatives thereof (U.S. Pat. No. 5,317,084; U.S. Pat. No. 5,304,633; European Patent Application No. 519,726 A2; European Patent Application No. 503,939 A1; PCT Application WO 93/22348, published Nov. 11, 1993; PCT Application WO 90/13642; and Tomita et al., In: *Lactoferrin Structure and Function,* Hutchens, T. W., et al., Eds., Plenum Press, NY, 1994, pp. 209–218); CEMA peptides or analogues or derivatives thereof (PCT Application WO 94/04688, published Mar. 3, 1994); tachyplesins and analogues of tachyplesins such as polyphemusins (Nakamura et al., 1988, *J. Biol. Chem.* 263:16709–16713; Miyata et al., 1989, *J. Biochem.* 106:663–668), defensins (Lehrer et al., 1991, *Cell* 64:229–230; Lehrer et al., 1993, *Ann. Rev.* *Immunol.* 11:105–128; U.S. Pat. No. 4,705,777; U.S. Pat. No. 4,659,692; U.S. Pat. No. 4,543,252), β-defensins (Selsted et al., 1993, *J. Biol. Chem.* 288:6641–6648; Diamond et al., 1991, *Proc. Natl. Acad. Sci. U.S.A.* 88:3952–3958), and protegrins (Kokryakov et al., 1993, FEBS 337:231–236; Zhao et al., 1994, *FEBS Letters* 346:285–288; Migorodskaya et al., 1993, *FEBS* 330:339–342; Storici et al., 1993, *Biochem. Biophys. Res. Commun.* 196:1363–1367; Zhao et al., 1994, *FEBS Lett.* 346:285–288; Manzoni et al., 1996, *FEBS Lett.* 383:93–98; U.S. Pat. No. 5,464,823).

Particularly preferred peptides are protegrin peptides, such as those described, for example in U.S. Pat. No. 5,464,823, WO 95/03325, and U.S. Ser. Nos. 08/451,832, 08/499,523, 08/562,346, 08/649,811 and 08/960,921. Thus, peptides suitable for use with the methods described herein will either be known to those of skill in the art or will be easily identified by way of tests commonly employed in the art, such as, for example, the tests provided in the examples. Generally, antimicrobial peptides useful in the methods of the invention will have minimum inhibitory concentrations (MICs) against Gram-positive and Gram-negative bacteria of less than about 128 μg/mL, preferably less than about 64 μg/mL and most preferably less than about 32 μg/mL as measured using the assays provided in the Examples. Alternatively, or in addition to, useful peptides will generally exhibit at least a two log reduction in oral colony forming units (CFUS) in saliva in 15 minutes at a peptide concentration of about 0.001% (w/w) to 5% (w/w).

In one illustrative embodiment of the invention, protegrin peptides useful for the treatment or prophylaxis of oral mucositis are peptides having the formula:

$$X_1-X_2-X_3-X_4-X_5-C_6-X_7-C_8-X_9-X_{10}-X_{11}-X_{12}-C_{13}-X_{14}-C_{15}-X_{16}-X_{17}-X_{18} \quad (I)$$

and its defined modified forms.

The designation $X_n$ in each case represents an amino acid at the specified position in the peptide. Similarly, the designation $C_n$ represents an amino acid at the specified position and further represents those positions in the peptides of formula (I) which may optionally contain amino acid residues capable of forming disulfide interlinkages.

The amino acid residues denoted by $X_n$ or $C_n$ may be the genetically encoded L-amino acids, naturally occurring non-genetically encoded L-amino acids, synthetic L-amino acids or D-enantiomers of all of the above. The amino acid notations used herein for the twenty genetically encoded L-amino acids and common non-encoded amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |

-continued

| Amino Acid | One-Letter Symbol | Common Abbreviation |
|---|---|---|
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Ornithine | O | Orn |
| β-alanine | | bAla |
| 2,3-diaminopropionic acid | | Dpr |
| α-aminoisobutyric acid | | Aib |
| N-methylglycine (sarcosine) | | MeGly |
| Citrulline | | Cit |
| t-butylalanine | | t-BuA |
| t-butylglycine | | t-BuG |
| N-methylisoleucine | | MeIle |
| phenylglycine | | Phg |
| cyclohexylalanine | | Cha |
| Norleucine | | Nle |
| 1-naphthylalanine | | 1-Nal |
| 2-naphthylalanine | | 2-Nal |
| 4-chlorophenylalanine | | Phe(4-Cl) |
| 2-fluorophenylalanine | | Phe(2-F) |
| 3-fluorophenylalanine | | Phe(3-F) |
| 4-fluorophenylalanine | | Phe(4-F) |
| Penicillamine | | Pen |
| 1,2,3,4-tetrahydro-isoquinoline-3-carboxylic acid | | Tic |
| β-2-thienylalanine | | Thi |
| Methionine sulfoxide | | MSO |
| Homoarginine | | Har |
| N-acetyl lysine | | AcLys |
| 2,4-diamino butyric acid | | Dbu |
| p-aminophenylalanine | | Phe(pNH$_2$) |
| N-methylvaline | | MeVal |
| Homocysteine | | hCys |
| Homoserine | | hSer |
| ε-amino hexanoic acid | | Aha |
| δ-amino valeric acid | | Ava |
| 2,3-diaminobutyric acid | | Dba |

Illustrative compounds useful in the methods of the invention are peptides which are partially defined in terms of amino acid residues of designated classes. Amino acid residues can be generally subclassified into major subclasses as follows:

Acidic: The residue has a negative charge due to loss of H$^+$ ion at physiological pH and the residue is attracted by aqueous solution so as to seek the surface positions in the conformation of a peptide in which it is contained when the peptide is in aqueous medium at physiological pH.

Basic: The residue has a positive charge due to association with H$^+$ ion at physiological pH and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Polar/large: The residues are not charged at physiological pH, but the residue is not sufficiently repelled by aqueous solutions so that it would necessarily seek an inner position in the conformation of the peptide in which it is contained when the peptide is in aqueous medium. Depending on the conditions, and on the remaining amino acids in the sequence, the residue may reside either in the inner space or at the surface of the protein.

Cysteine-Like: Residues having a side chain capable of participating in a disulfide linkage. Thus, cysteine-like amino acids generally have a side chain containing at least one thiol (SH) group, such as cysteine, homocysteine, penicillamine, etc.

Small: Certain neutral amino acids having side chains that are not sufficiently large, even if polar groups are lacking, to confer hydrophobicity. "Small" amino acids are those with four carbons or less when at least one polar group is on the side chain and three carbons or less when not.

The gene-encoded secondary amino acid proline (as well as proline-like imino acids such as 3-hydroxyproline and 4-hydroxyproline) is a special case due to its known effects on the secondary conformation of peptide chains, and is not, therefore, included in a group.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues.

Certain commonly encountered amino acids which are not genetically encoded of which the peptides of the invention may be composed include, but are not limited to, β-alanine (b-Ala) and other omega-amino acids such as 3-aminopropionic acid, 2,3-diaminopropionic acid. (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 1-naphthylalanine (1-Nal); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (Har); N-acetyl lysine (AcLys); 2,3-diaminobutyric acid (Dab); 2,4-diaminobutyric acid (Dbu); p-aminophenylalanine (Phe(pNH$_2$)); N-methyl valine (MeVal); homocysteine (hCys) and homoserine (hSer). These amino acids also fall conveniently into the categories defined above.

The classifications of the above-described genetically encoded and non-encoded amino acids are summarized in Table 1, below. It is to be understood that Table 1 is for illustrative purposes only and does not purport to be an exhaustive list of amino acid residues that may comprise the illustrative peptides described herein.

TABLE 1

Amino Acid Classifications

| Classification | Genetically Encoded | Non-Genetically Encoded |
|---|---|---|
| Hydrophobic | Y, V, I, L, M, F, W | Phg, 1-Nal, 2-Nal, Thi, Tic, Phe (4-Cl), Phe (2-F), Phe (3-F), Phe (4-F), t-BuA, t-BuG, MeIle, Nle, MeVal, Cha |
| Acidic | D, E | |
| Basic | H, K, R | Dpr, Orn, hArg, Phe(p-NH$_2$), Dbu, Dab |
| Polar/Large | Q, N | Cit, AcLys, MSO |
| Small | G, S, A, T | bAla, MeGly, Aib, hSer |
| Cysteine-Like | C | Pen, hCys |

In the peptides of formula I, the symbol "—" between amino acid residues $X_n$ and/or $C_n$ generally designates a backbone interlinkage. Thus, the symbol "—" usually designates an amide linkage (—C(O)—NH). It is to be understood, however, that in many of the peptides useful in the methods of the invention one or more amide linkages may optionally be replaced with a linkage other than amide. Such linkages include, but are not limited to, —CH$_2$NH—, —CH$_2$S—, —CH$_2$CH$_2$, —CH=CH— (cis and trans), —C(O)CH$_2$—, —CH(OH)CH$_2$— and —CH$_2$SO—.

Peptides having such linkages and methods for preparing such peptides are well-known in the art (see, e.g., Spatola, 1983, *Vega Data* 1(3) (general review); Spatola, 1983, "Peptide Backbone Modifications" In: *Chemistry and Biochemistry of Amino Acids Peptides and Proteins* (Weinstein, ed.), Marcel Dekker, New York, p. 267 (general review); Morley, 1980, *Trends Pharm. Sci.* 1:463–468; Hudson et al., 1979, *Int. J. Prot. Res.* 14:177–185 (—CH$_2$NH—, —CH$_2$CH$_2$—); Spatola et al., 1986, Life Sci. 38:1243–1249 (—CH$_2$—S); Hann, 1982, J. Chem. Soc. Perkin Trans. I. 1:307–314 (—CH=CH—, cis and trans); Almquist et al., 1980, *J. Med. Chem.* 23:1392–1398 (—COCH$_2$—); Jennings-White et al., *Tetrahedron. Lett.* 23:2533 (—COCH$_2$—); European Patent Application EP 45665 (1982) CA:97:39405 (—CH(OH)CH$_2$—); Holladay et al., 1983, *Tetrahedron Lett.* 24:4401–4404 (—C(OH)CH$_2$—); and Hruby, 1982, *Life Sci.* 31:189–199 (—CH$_2$—S—).

The peptides of the invention are characterized by a structure containing two main elements or motifs: a reverse-turn region bracketed by two strands that form an anti-parallel β-sheet. While not intending to be bound by theory, it is believed that the antimicrobial activity of the compounds of formula (I) is in part associated with such a core structure.

The β-sheet region of the peptides comprises an N-strand (residues $X_1$—$C_8$) and a C-strand (residues $C_{13}$—$X_{18}$). The N-strand and C-strand are arranged anti-parallel to one another and are non-covalently linked together via backbone-backbone hydrogen bonds (for a detailed description of the structure of β-sheets the reader is referred to Creighton, 1993, *Protein Structures and Molecular Properties*, W. H. Freeman and Co., NY, and references cited therein). While not intending to be bound by theory, it is believed that the most important residues for β-sheet formation are $X_5$—$C_8$ and $C_{13}$—$X_{16}$.

Preferably, the β-sheet region of the peptides is amphiphilic, i.e., one surface of the β-sheet has a net hydrophobic character and the other surface has a net hydrophilic character. Referring to the β-sheet structure illustrated in FIG. 7, the side chains of L-amino acid residues adjacent to one another intrastrand-wise (residues n, n+1, n+2, etc.) point in opposite directions so as to be positioned on opposite surfaces of the β-sheet. The side chains of L-amino acid residues adjacent to one another interstrand-wise (residues n and c, n+1 and c+1, etc.) point in the same direction so as to be positioned on the same surface of the β-sheet. Using this general structural motif an amphiphilic antiparallel β-sheet is obtained by selecting amino acids at each residue position so as to yield a β-sheet having hydrophobic side chains positioned on one surface of the sheet and hydrophilic side chains positioned on the other.

Of course, it will be appreciated that as the surfaces of the amphiphilic anti-parallel β-sheet region need only have net hydrophobic or net hydrophilic character, each side chain comprising a particular surface need not be hydrophobic or hydrophilic. The surfaces may contain side chains that do not significantly alter the net character of the surface. For example, both the hydrophobic and hydrophilic surfaces may contain small amino acid side chains, as these side chains do not significantly contribute to the net character of the surface.

The β-sheet region of the peptides of formula I may contain from one to four cysteine-like amino acids, designated $C_6$, $C_8$, $C_{13}$ and $C_{15}$, which may participate in interstrand disulfide bonds. Peptides that contain at least two cysteine-like amino acid residues may be in straight-chain or cyclic form, depending on the extent of disulfide bond formation. The cyclic forms are the result of the formation of disulfide linkages among all or some of the four invariant cysteine-like amino acids. Cyclic forms of the invention include all possible permutations of disulfide bond formation. The straight-chain forms are convertible to the cyclic forms, and vice versa. Methods for forming disulfide bonds to create the cyclic peptides are well known in the art, as are methods to reduce disulfides to form the linear compounds.

The native forms of the protegrins contain two disulfide bonds; one between cysteine $C_6$–$C_{15}$ and another between cysteine $C_8$–$C_{13}$ (Harwig et al., 1995, *J. Peptide Sci.* 3:207). Accordingly, in those embodiments having two disulfide linkages, the $C_6$–$C_{15}$, $C_8$–$C_{13}$ form is preferred. Such peptides are designated "native" forms. However, it has been found that forms of the protegrins containing only one disulfide linkage are active and easily prepared. Preferred among embodiments having only one disulfide linkage are those represented by $C_6$–$C_{15}$ alone and by $C_8$–$C_{13}$ alone.

Forms containing a $C_6$–$C_{15}$ disulfide as the only disulfide linkage are generally designated "bullet" forms of the protegrins; those wherein the sole disulfide is $C_8$–$C_{13}$ are designated the "kite" forms. The bullet and kite forms can most conveniently be made by replacing each of the cysteine-like amino acid residues at the positions that are not involved in a disulfide linkage with amino acids that do not participate in disulfide bonds, preferably with small amino acids such as glycine, serine, alanine or threonine. Alternatively, $C_8$ and/or $C_{13}$ may be absent.

As the linear or "snake" forms of the native peptides have valuable activities, the peptides of the invention include linearized forms wherein the sulfhydryl (SH) groups are chemically stabilized with suitable reagents. As defined herein, "SH-stabilized" forms of the peptides of the invention contain sulfhydryl groups that have been reacted with standard reagents to prevent reformation of disulfide linkages or forms wherein the cysteine-like amino acid residues are replaced by other amino acids as set forth above. It is preferred that all four cysteine-like amino acid residues be SH-stabilized or replaced in order to minimize the likelihood of the formation of intermolecular disulfide linkages.

The sulfur atoms involved in an interstrand disulfide bridge in a β-sheet are not positioned within the plane defined by the interstrand backbone-backbone hydrogen-bonds; the sulfur atoms are at an angle with respect to the β-carbons of the bridged amino acid residues so as to be positioned on a surface of the β-sheet. Thus, the sulfur atoms of the disulfide linkages contribute to the net hydrophilicity of a surface of the β-sheet. It is to be understood that in the peptides of formula I a β-sheet region defined by the following formula is specifically contemplated to fall within the definition of amphiphilic antiparallel sheet as described herein:

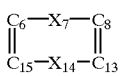

wherein $C_6$, $C_8$, $C_{13}$ and $C_{15}$ are each independently a cysteine-like amino acid, $X_7$ and $X_{14}$ are each independently a hydrophobic or small amino acid and ‖ is a disulfide bond. In a particularly preferred embodiment, $C_6$, $C_8$, $C_{13}$ and $C_{15}$ are each cysteine and $X_7$ and $X_{14}$ are each independently hydrophobic amino acids.

Figure 7:
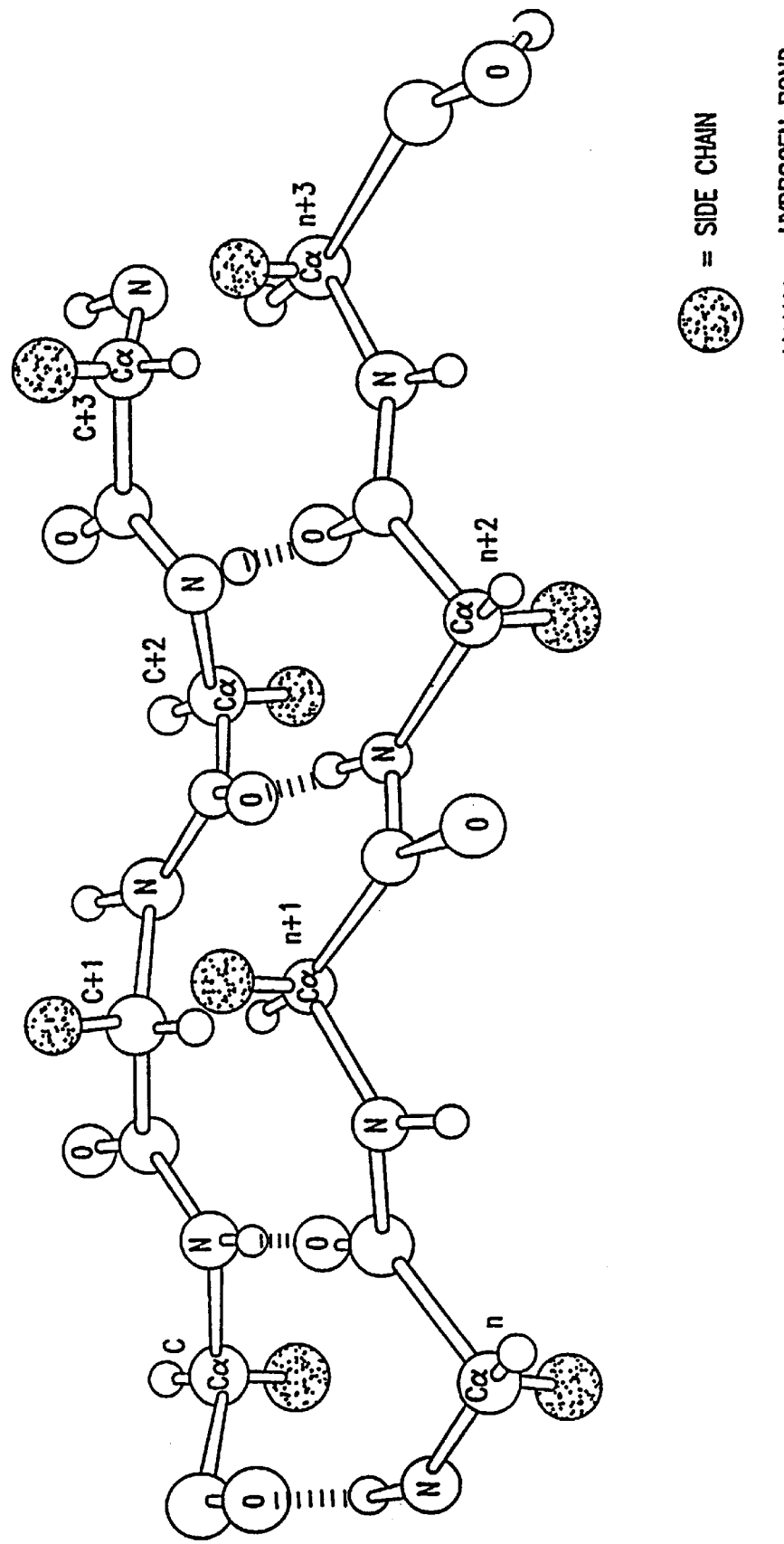
FIG. 7 is an illustration of a peptide β-sheet secondary structure.

The β-sheet secondary structure illustrated in FIG. 7 is composed entirely of L-amino acids. Those having skill in the art will recognize that substituting an L-amino acid with its corresponding D-enantiomer at a specific residue position may disrupt the structural stability or amphiphilicity of the amphiphilic anti-parallel β-sheet region. The degree to which any particular enantiomeric substitution disrupts the structural stability or amphiphilicity depends, in part, on the size of the amino acid side chain and position of the residue within the β-sheet. Preferably, the β-sheet region of the peptides of formula I will contain mixtures of L- and D-amino acids that do not significantly affect the stability or amphiphilicity of the β-sheet region as compared to peptides containing the corresponding all D- or all L-enantiomeric forms of the sheet. Enantiomeric substitutions that do not substantially affect the stability or amphiphilicity of the β-sheet region will be readily apparent to those having skill in the art.

In a preferred embodiment of the invention, hydrophobic, basic, polar/large and cysteine-like amino acids comprising the β-sheet region are either all L-enantiomers or all D-enantiomers. Small amino acids comprising the β-sheet region may be either L-enantiomers or D-enantiomers.

The reverse-turn region of the peptides of formula I (residues $X_9$—$X_{10}$—$X_{11}$—$X_{12}$ taken together) links the strands of the anti-parallel β-sheet. Thus, the reverse-turn region comprises a structure that reverses the direction of the polypeptide chain so as to allow a region of the peptide to adopt an anti-parallel β-sheet secondary structure.

The reverse-turn region of the molecule generally comprises two, three or four amino acid residues (residue $X_9$ and/or $X_{12}$ may be absent). An important feature of the illustrative protegrin peptides described herein is the presence of a positive charge in the turn region of the molecule. Thus, one of $X_9$–$X_{12}$, preferably two of $X_9$–$X_{12}$, must be a basic amino acid. Such two, three and four amino acid segments capable of effecting a turn in a peptide are well known and will be apparent to those of skill in the art.

In a preferred embodiment of the invention, the reverse-turn is a three amino acid residue γ-turn. Virtually any γ-turn sequence known in the art may be used in the peptides described herein, including those described, for example, in Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 203:221–232; Sibanda et al., 1989, *J. Mol. Biol* 206:759–777; and Tramontano et al., 1989, *Proteins: Struct. Funct. Genet.* 6:382–394.

In another preferred embodiment the reverse-turn is a four amino acid residue β-turn. In such structures, the two internal amino acid residues of the turn are usually not involved in the hydrogen-bonding of the anti-parallel β-sheet; the two amino acid residues on either side of the internal residues are usually included in the hydrogen-bonding of the β-sheet. While not intending to be bound by theory, it is believed that such hydrogen bonding helps stabilize the β-sheet region of the molecule.

The conformations and sequences of many peptide β-turns have been well-described in the art and include, by way of example and not limitation, type-I, type-I', type-II, type-II', type-III, type-III', type-IV, type-V, type-V', type-VIa, type-VIb, type-VII and type-VIII (see, Richardson, 1981, *Adv. Protein Chem.* 34:167–339; Rose et al., 1985, *Adv. Protein Chem.* 37:1–109; Wilmot et al., 1988, *J. Mol. Biol.* 203:221–232; Sibanda et al., 1989, *J. Mol. Biol.* 206:759–777; Tramontano et al., 1989, *Proteins: Struct. Funct. Genet.* 6:382–394). All of these types of peptide β-turn structures and their corresponding sequences, as well as later discovered peptide β-turn structures and sequences, are specifically contemplated by the invention.

The specific conformations of short peptide turns such as β-turns depend primarily on the positions of certain amino acid residues in the turn (usually Gly, Asn or Pro). Generally, the type-I β-turn is compatible with any amino acid residue at positions $X_9$ through $X_{12}$, except that Pro cannot occur at position $X_{11}$. Gly predominates at position $X_{12}$ and Pro predominates at position $X_{10}$ of both type-I and type-II turns. Asp, Asn, Ser and Cys residues frequently occur at position $X_9$, where their side chains often hydrogen-bond to the NH of residue $X_{11}$.

In type-II turns, Gly and Asn occur most frequently at position $X_{11}$, as they adopt the required backbone angles most easily. Ideally, type-I' turns have Gly at positions $X_{10}$ and $X_{11}$, and type-II' turns have Gly at position $X_{10}$. Type-III turns generally can have most amino acid residues, but type-III' turns usually require Gly at positions $X_{10}$ and $X_{11}$.

Type-VIa and VIb turns generally have a cis peptide bond and Pro as an internal residue. For a review of the different types and sequences of β-turns in proteins and peptides the reader is referred to Wilmot et al., 1988, *J. Mol. Biol.* 203:221–232.

Preferred β-turn sequences include those wherein $X_9$ is a basic amino acid (preferably R, K, Orn or Dab) or a hydrophobic amino acid (preferably W, F, Y or Cha); $X_{10}$ is a basic amino acid (preferably R), a small amino acid (preferably MeGly) or proline; $X_{11}$ is a basic amino acid (preferably R, K, Orn or Dab) or a hydrophobic amino acid (preferably W, F, Y or Cha); and $X_{12}$ is a hydrophobic amino acid (preferably W, F, Y, I or Cha).

The protegrin peptides useful in the methods of the invention are generally basic, i.e., they have a net positive charge at physiological pH. While not intending to be bound by theory, it is believed that the presence of positively charged amino acid residues, particularly in the turn region of the molecule, is important for antimicrobial activity.

It is understood that in a statistical collection of individual amino acid residues in a structure such as a peptide some of the amino acid residues will be positively charged, some negatively charged and some uncharged. Thus, some of the peptides will have a charge and some not. To fit the definition of "basic," an excess of amino acid residues in the peptide molecule are positively charged at physiological pH.

Thus, approximately 15% but no more than up to about 50% of the amino acids must be basic amino acids, and the compounds must have a net charge of at least +1 at physiological pH. Preferably, the illustrative peptides will have a net charge of at least +3 at physiological pH.

For embodiments having as few as 10 amino acids, there may be only one basic amino acid residue; however, at least two basic residues, even in this short-chain residue, are preferred. If the protegrin peptide contains as many as 15 amino acid residues, two basic residues are required. It is preferred that at least 20% of the amino acids in the sequence be basic, with 30% basic amino acids being particularly preferred.

The amino terminus of the illustrative peptides may be in the free amino form or may be acylated by a group of the formula RCO—, wherein R represents a hydrocarbyl group of 1–25C, preferably 1–10C, more preferably 1–8C. The hydrocarbyl group can be saturated or unsaturated, straight chain, branched or cyclic, and is typically, for example, methyl, ethyl, isopropyl, t-butyl, n-pentyl, cyclohexyl, cyclohexene-2-yl, hexene-3-yl, hexyne-4-yl, octyl, decyl, eicanosyl and the like.

Alternatively, the amino terminus may be substituted with aromatic groups such as naphthyl, etc. Such peptides can be conveniently prepared by incorporating appropriate amino acids, such as 1-naphthylalanine and 2-naphthylalanine at the N-terminus of the peptide.

The amino terminus of the peptides may also be substituted to use solute-specific transmembrane channels to facilitate their entry into the bacterial periplasm. For example, the peptides can be conveniently modified at the N-terminus with catechol using catechol-NHS activated ester.

The C-terminus of peptides useful in the methods described herein may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, $RNH_2$, or $R_2NH$, wherein each R is independently hydrocarbyl of 1–25C as defined and with preferred embodiments as above. Amidated forms of the peptides wherein the C-terminus has the formula $CONH_2$ are preferred.

Thus, certain illustrative protegrin peptides useful in the methods of the invention are peptides having the formula:

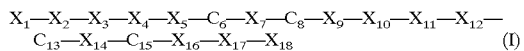   (I)

or pharmaceutically acceptable salts thereof, and its defined modified forms wherein:

each of $C_8$ and $C_{13}$ is independently present or not present, and if present each is independently a cysteine-like, basic, small, polar/large or hydrophobic;

each of $C_6$ and $C_{15}$ is independently a cysteine-like, basic, small, polar/large or hydrophobic amino acid;

each of $X_1$–$X_5$ is independently present or not present, and if present each is independently a basic, hydrophobic, polar/large, or small amino acid;

each of $X_7$ and $X_{14}$ is independently a hydrophobic or a small amino acid;

each of $X_9$ and $X_{12}$ is independently present or not present;

$X_9$–$X_{12}$ taken together are capable of effecting a reverse turn when contained in the amino acid sequence of formula (I) and at least one of $X_9$–$X_{12}$ must be a basic amino acid;

each of $X_{16}$–$X_{18}$ is independently present or not present, and if present each is independently a basic, hydrophobic, polar/large or small amino acid;

and wherein at least about 15% up to about 50% of the amino acids comprising said antimicrobial peptide are basic amino acids such that said antimicrobial peptide has a net charge of at least +1 at physiological pH.

In a preferred embodiment, the illustrative peptides have the formula:

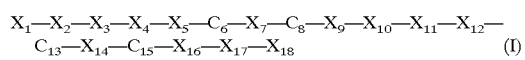   (I)

or pharmaceutically acceptable salts thereof, wherein:

$X_1$ is either present or absent, and if present is a basic amino acid;

$X_2$ is either present or absent, and if present is a small, basic or hydrophobic amino acid;

$X_3$ is either present or absent, and if present is a small or hydrophobic amino acid;

$X_4$ is either present or absent, and if present is a small, basic or hydrophobic amino acid;

$X_5$ is a small, basic or hydrophobic amino acid;

$C_6$ is a cysteine-like amino acid;

$X_7$ is a small or hydrophobic amino acid;

$C_8$ is a cysteine-like, small, basic or hydrophobic amino acid;

$X_9$ is a basic or hydrophobic amino acid;

$X_{10}$ is a small or basic amino acid or proline;

$X_{11}$ is a basic or hydrophobic amino acid;

$X_{12}$ is a hydrophobic amino acid $C_{13}$ is a cysteine-like, small, basic or hydrophobic amino acid;

$X_{14}$ is a small or hydrophobic amino acid;

$C_{15}$ is a cysteine-like amino acid;

$X_{16}$ is either present or absent, and if present is a hydrophobic amino acid;

$X_{17}$ is either present or absent, and if present is a small amino acid; and $X_{18}$ is either present or absent, and if present is a basic amino acid.

Particularly preferred peptides are those wherein $X_1$ is R; $X_2$ is absent or R, G or L; $X_3$ is absent or G, L, W or Cha; $X_4$ is absent or R, G or W; $X_5$ is R, G, A, L, V, W or Cha; $C_6$ is C; $X_7$ is A, Y, F or Cha; $C_8$ is C, K, A or T; $X_9$ is R, F, W, Y or L; $X_{10}$ is R, G, MeGly or P; $X_{11}$ is R, W, F or Cha; $X_{12}$ is F, I, Y, W or Cha; $C_{13}$ is C, K, A or T; $X_{14}$ is G, A, V or F; $C_{15}$ is C; $X_{16}$ is absent or V, F; $X_{17}$ is absent or G; and $X_{18}$ is absent or R.

In another particularly preferred embodiment of the invention, the peptide of formula (I) is selected from the group consisting of:

| | | | |
|---|---|---|---|
| (OM-1) | RGGRLCYCRRRFCVCVGR | | (SEQ ID NO: 1) |
| (OM-2) | RGGRLCYCRRRFCVCVGR* | | (SEQ ID NO: 2) |
| (OM-3) | RGGLCYCRGRFCVCVGR | | (SEQ ID NO: 3) |
| (OM-4) | RLLRACYCRXRFCVCVGR | (X = MeGly) | (SEQ ID NO: 4) |
| (OM-5) | RGGRLCYCRPRFCVCVGR | | (SEQ ID NO: 5) |
| (OM-6) | RGGGLCYKRGWIKFCVGR | | (SEQ ID NO: 6) |
| (OM-7) | RGWGLCYCRPRFCVCVGR | | (SEQ ID NO: 7) |
| (OM-8) | RLCYCRPRFCVCVGR | | (SEQ ID NO: 8) |
| (OM-9) | RGGGLCYTRPRFTVCVGR | | (SEQ ID NO: 9) |
| (OM-10) | LCYCRGRFCVCVGR | | (SEQ ID NO: 10) |
| (OM-11) | RWRLCYCRPRFCVCV | | (SEQ ID NO: 11) |
| (OM-12) | RGWRLCYCRPRFCVCVGR | | (SEQ ID NO: 12) |
| (OM-13) | RGWRACYCRPRFCACVGR | | (SEQ ID NO: 13) |
| (OM-14) | GWRLCYCRPRFCVCVGR | | (SEQ ID NO: 14) |
| (OM-15) | XCYCRRRFCVCV | (X = Cha) | (SEQ ID NO: 15) |
| (OM-16) | WLCYCRRRFCVCV* | | (SEQ ID NO: 16) |
| (OM-17) | RLCYCRXRFCVCV | (X = MeGly) | (SEQ ID NO: 17) |
| (OM-18) | RLCYCRPRFCVCVGR* | | (SEQ ID NO: 18) |
| (OM-19) | RGGGLCYCRPRFCVCVGR* | | (SEQ ID NO: 19) |
| (OM-20) | RXCFCRPRFCVCV | (X = Cha) | (SEQ ID NO: 20) |
| (OM-21) | RWCFCRPRFCVCV | | (SEQ ID NO: 21) |
| (OM-22) | LCXCRRRXCVCV | (X = Cha) | (SEQ ID NO: 22) |
| (OM-23) | RGGRLCYCRRRFCVC | | (SEQ ID NO: 23) |
| (OM-24) | LCYTRRRFTVCV | | (SEQ ID NO: 24) |
| (OM-25) | RRCYCRRRFCVCVGR | | (SEQ ID NO: 25) |
| (OM-26) | RLCYCRRRFCVCV* | | (SEQ ID NO: 26) |
| (OM-27) | RXRLCYCRZRFCVCV | (X = Cha)<br>(Z = MeGly) | (SEQ ID NO: 27) |
| (OM-28) | RGWRLCYCRGRXCVCV | (X = Cha) | (SEQ ID NO: 28) |
| (OM-29) | RGLRXCYCRGRFCVCVGR | (X = Cha) | (SEQ ID NO: 29) |
| (OM-30) | RGWRGCYKRGRFKGCVGR | | (SEQ ID NO: 30) |
| (OM-31) | RGWRGCYCRXRFCGC | (X = MeGly) | (SEQ ID NO: 31) |
| (OM-32) | RGGLCYCRGRFCVCVGR | | (SEQ ID NO: 32) |
| (OM-33) | RLLRLCYCRXRFCVCVGR | (X = MeGly) | (SEQ ID NO: 33) |
| (OM-34) | RGGRLCYCRGRFCVCVGR* | | (SEQ ID NO: 34) |
| (OM-35) | RGWRLCYCRGRFCVCVGR | | (SEQ ID NO: 35) |
| (OM-36) | RGGRLCYCRGRFCVCVGR | | (SEQ ID NO: 36) |
| (OM-37) | RGGRVCYCRGRFCVCVGR | | (SEQ ID NO: 37) |
| (OM-38) | RGGRVCYCRGRFCVCV | | (SEQ ID NO: 38) |
| (OM-39) | RGGRVCYCRGRFCVCV* | | (SEQ ID NO: 39) |
| (OM-40) | WLCYCRRRFCVCV | | (SEQ ID NO: 40) |
| (OM-41) | RGGGLCYARGWIAFCVCVGR | | (SEQ ID NO: 41) |
| (OM-42) | LCYCRRRFCVCVF | | (SEQ ID NO: 42) |
| (OM-43) | RLCYCRPRFCVCV | | (SEQ ID NO: 43) |
| (OM-44) | RLCACRGRACVCV | | (SEQ ID NO: 44) | where peptides denoted with * are acid forms and all others are amide forms.

Methods of Preparation

Certain peptides useful in the methods of the invention, such as naturally occuring PG-1 (SEQ ID NO:1) through PG-5 (SEQ ID NO:5) can be isolated from procine leukocytes as described in U.S. Pat. No. 5,464,823. All of the peptides can be chemically synthesized using standard art-known techniques. The N- and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

At the carboxyl terminus, the carboxyl group may, of course, be present in the form of a salt; in the case of pharmaceutical compositions this will be a pharmaceutically acceptable salt, as previously described. The carboxyl terminus may also be esterified using alcohols of the formula ROH wherein R is hydrocarbyl (1–6C) as defined above. Similarly, the carboxyl terminus may be amidated so as to have the formula —CONH$_2$, —CONHR, or —CONR$_2$, wherein each R is independently hydrocarbyl (1–6C) as herein defined. Techniques for esterification and amidation as well as for neutralizing in the presence of base to form salts are all standard organic chemical techniques.

Preferred methods of synthesis of peptides having a C-terminal amide are provided in the Examples.

Formation of disulfide linkages, if desired, is conducted in the presence of mild oxidizing agents. Chemical oxidizing agents may be used, or the compounds may simply be exposed to the oxygen of the air to effect these linkages. Various methods are known in the art. Processes useful for disulfide bond formation have been described by Tam, J. P. et al., *Synthesis* (1979) 955–957; Stewart, J. M. et al., *Solid Phase Peptide Synthesis,* 2d Ed. Pierce Chemical Company Rockford, Ill. (1984); Ahmed A. K. et al., *J Biol Chem* (1975) 250:8477–8482 and Pennington M. W. et al., *Peptides* 1990, E. Giralt et al., ESCOM Leiden, The Netherlands (1991) 164–166. An additional alternative is described by Kamber, B. et al., *Helv Chim Acta* (1980) 63:899–915. A method conducted on solid supports is described by Albericio *Int J Pept Protein Res* (1985) 26:92–97. A particularly preferred method is solution oxidation using molecular oxygen, as described in the Examples.

Alternatively, the sulfhydryl groups of cysteine-like amino acids can be stabilized by reacting with alkylating agents using well-known methods.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host.

Recombinantly produced forms of the protegrins may require subsequent derivatization to modify the N- and/or C-terminus and, depending on the isolation procedure, to effect the formation of disulfide bonds as described hereinabove. Depending on the host organism used for recombinant production and the animal source from which the protein is isolated, some or all of these conversions may already have been effected.

For recombinant production, the DNA encoding the protegrins of the invention is included in an expression system which places these coding sequences under control of a suitable promoter and other control sequences compatible with an intended host cell. Types of host cells available span almost the entire range of the plant and animal kingdoms. Thus, the protegrins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-à-vis these infective agents.

Suitable recombinant methods and expression systems will be apparent to those of skill in the art.

Administration

The methods of the invention generally involve topically applying to the oral cavity of the subject being treated an amount of an antimicrobial protegrin peptide effective to treat or prevent oral mucositis. A therapeutically effective dose refers to that amount of protegrin peptide sufficient to result in amelioration of symptoms associated with oral mucositis and/or in a reduction in the mouth of the subject of the number colony forming units ("CFUs") of flora associated with oral mucositis as compared to the number of CFUs observed prior to treatment. Typically, a reduction of CFUs on the order of 3–4 log is considered to be therapeutically effective, however, even reductions on the order of 1–2 log may provide significant amelioration of symptoms, and hence therapeutic benefit.

It has been discovered that in addition to providing therapeutic benefit to patients suffering from oral mucositis, the protegrins are particularly effective when used prophylactically. Thus, a therapeutically effective dose also refers to an amount of protegrin peptide sufficient to prevent the onset of oral mucositis. Accordingly, the prophylactic use of protegrin peptides in patients at risk for developing oral mucositis, such as those receiving chemotherapy or radiotherapy, is an important aspect of the invention.

For any protegrin peptide a therapeutically effective dose can be estimated initially from in vitro tests such as, for example, MICs and saliva kill kinetics. Initial dosages can also be estimated from in vivo data, e.g., animal models, using techniques that are well known in the art. A particularly effective preclinical animal model for estimating dosages effective to treat or prevent oral mucositis is the hamster model (Sonis et al., 1990, *oral Surg. Oral Med. Oral Pathol.* 69:437–443; Sonis et al., 1995, *Oral Oncol. Eur. J. Cancer* 31B:261–266). One having ordinary skill in the art could readily optimize administration to humans based on animal data, especially in light of the detailed disclosure herein.

In general, the protegrin peptides will be most beneficial when applied to the oral cavity before oral mucositis occurs. Thus, in general, treatment will begin when a patient is considered to be at high risk for developing mucositis. Of course, whether and when a patient is considered to be at high risk will depend on such factors as the age of the patient, the aggressiveness of the chemo- or radiotherapy, the type of tumor or cancer being treated, and the chemotherapeutic agent being used. A treating physician will be able to determine when a particular patient is at high risk for developing mucositis. However, the protegrin peptides may be applied when the patient begins to feel oral inflammation, or even after lesions have appeared.

As will be discussed in more detail below, the protegrins will typically be administered in the form of a topical oral formulation. Such formulations will generally comprise about 0.001% (w/w) to 2.5% (w/w) active ingredient; however, concentration ranges such as 0.005% (w/w) to 0.75% (w/w) or even 0.03% (w/w) to 0.3% (w/w) are expected to be effective.

The protegrins may be applied topically several times per day, depending in part on the concentration of the applied dose and the frequency of food and fluid intake by the patient. Thus, depending on the particular circumstances, the protegrins may be applied 2, 3, 4 or even as many as 6 times per day. A saline rinse prior to each application and restriction of food and fluid intake for at least 30 minutes and up to about several hours after application may enhance the effectiveness of treatment. Preferably, the protegrin treatment will be administered for about 1–4 weeks, but treatment regimens as short as 3–4 days may also provide prophylactic or therapeutic benefit. In some instances, it may be desirable to treat the patient for the entire period during which the patient receives chemotherapy and/or radiotherapy.

The actual amount of antimicrobial peptide administered as well as the dosing schedule of peptide administered will, of course, depend on factors such as the age of the patient, the severity of the affliction, the aggressiveness of chemotherapy or radiotherapy being pursued, and, of course, on the judgement of the prescribing physician.

The protegrins can be administered singly or in admixture with other protegrins or antimicrobial peptides or other agents, including, for example, painkillers (lidocaine, etc.) or anti-inflammatories.

Formulation

Typically, the peptides are applied to the oral cavity in the form of a topical pharmaceutical formulation. Formulations suitable for topical oral application include oral emulsions, magmas, gels, swishes, lozenges, pastes, creams, oral solutions, gums, etc., as are well known in the art. Any of these topical oral vehicles can be used in conjunction with the methods of the invention. Exact formulations, as well as methods of their preparation, will be apparent to those of skill in the art (see, e.g., Ansel et al., 1995, *Pharmaceutical Dosage Forms and Drug Delivery*, Williams & Wilkins, Malvern, Pa.; *Remington's Pharmaceutical Sciences*, latest edition, Mack Publishing Co., Easton, Pa.).

In a preferred embodiment of the invention, the peptides are administered in a topical gel-like formulation comprising about 0.001% (w/w) to 2.5% (w/w), preferably about 0.005% (w/w) to 0.75% (w/w), more preferably about 0.03% (w/w) to 0.3% (w/w) and most preferably about 0.025% (w/w) to 0.15% (w/w) active peptides(s) in admixture with a gel-like vehicle. The gel-like vehicle generally comprises a water-soluble gelling agent, a humectant and water, and has a viscosity of about 500 to 100,000 cps, preferably about 10,000 to 50,000 cps, more preferably about 15,000 to 30,000 cps and most preferably about 20,000 to 25,000 cps as measured with a Brookfield viscometer at about 25° C. The gelling agent provides the formulation with good mucoadhesion properties; the humectant with good moisturizing and moisture-barrier properties.

Gelling agents suitable for use with the vehicle of the invention include, e.g., agar, bentonite, carbomer (e.g., carbopol), water soluble cellulosic polymers (e.g., carboxyalkyl cellulose, hydroxyalkyl cellulose, alkyl cellulose, hydroxyalkyl alkylcellulose), povidone, kaolin, tragacanth and veegum, with hydroxylalkyl alkyl celluloses such as hydroxypropyl methylcellulose being preferred.

Humectants suitable for use with the gel-like vehicle of the invention include, e.g., glycerin, propylene glycol and sorbitol, with sorbitol being preferred.

Generally, the vehicle comprises about 0.1% (w/w) to 10% (w/w) water-soluble gelling agent, with about 0.25% (w/w) to 5% (w/w) being preferred and about 0.5% (w/w) to 3% (w/w) being most preferred and about 0.1% (w/w) to 20% (w/w) humectant. However, as the viscosity of the gel-like vehicle is of considerable importance, it will be understood that the above concentration ranges are for guidance only. The actual concentration of gelling agent will depend, in part, on the polymer selected, the supplier and the specific lot number. The actual concentrations of other ingredients will likeise affect the viscosity of the gel-like formulation. Choosing appropriate concentrations to yield a gel-like formulation with the desirable viscosity and other properties described herein is within the capabilities of ordinarily skilled artisans.

Additionally, the gel-like vehicle of the invention may include antimicrobial preservatives. Antimicrobial preservatives useful with the compositions of the invention include, but are not limited to, antifungal preservatives such as benzoic acid, alkylparabens, sodium benzoate and sodium propionate; and antimicrobial preservatives such as benzalkonium chloride, benzethonium chloride, benzyl alcohol, cetylpyridinium chloride, chlorobutanol, phenol, phenylethyl alcohol, phenylmercuric nitrate and thimerosal, with alkylparabens such as methylparaben, propylparaben and mixtures thereof being preferred.

An amount of antimicrobial preservative(s) effective for use with the formulations of the invention will be apparent to those of skill in the art and will depend, in part, on the antimicrobial agent(s) used. Typical concentrations range from about 0.01% (w/w) to about 2% (w/w).

The composition of the invention may also contain from about 1% (w/w) to 10% (w/w) of a sweetening agent such as aspartame, dextrose, glycerin, malitol, mannitol, saccharin sodium, sorbitol, sucrose and xylitol. Such sweetening agents are believed to aid patient compliance.

Of course, the pH of the composition will depend on the active ingredient(s) contained in the composition. Determination of an optimal pH for stability and effectivity is well within the skill of the ordinary artisan.

Other optional ingredients that can be used without deleteriously affecting, and in some cases even enhancing, the efficacy of the formulations of the invention include, but are not limited to, acidifying agents such as acetic acid, citric acid, fumaric acid, hydrochloric acid, lactic acid and nitric acid; alkalinizing agents such as ammonia solution, ammonium carbonate, diethanolamine, monoethanolamine, potassium hydroxide, sodium borate, sodium carbonate, sodium hydroxide, triethanolamine and trolamine; buffering agents such as potassium metaphosphate, potassium phosphate, sodium acetate and sodium citrate; antioxidants such as ascorbic acid, ascorbyl palmitate, butylated hydroxyanisole, butylated hydroxytoluene, hypophosphorous acid, monothioglyceride, propyl gallate, sodium ascorbate, sodium bisulfite, sodium formaldehyde sulfoxylate and sodium metabisulfite; chelating agents such as edetate disodium and edetic acid; colorants such as FD&C Red No. 3, FD&C Red No. 20, FD&C Yellow No. 6, FD&C Blue No. 2, D&C Green No. 5, D&C Orange No. 5, caramel and ferric oxide, red; and flavoring agents such as anise oil, cinnamon oil, cocoa, menthol, orange oil, peppermint oil vanillin. Suitable concentrations for use will be apparent to those of skill in then art. Other optional ingredients, as well as suitable concentrations for use, can be found, for example, in *Remington's Pharmaceutical Sciences,* latest edition, Mack Publishing Co., Easton, Pa.

EXAMPLE 1

Synthesis of Peptides PG-1 and OM-3

This Example describes preferred methods of synthesizing peptides of the invention having a C-terminal amide.

1.1 Synthesis of Linear Peptide

Linear amidated forms of peptides PG-1 and OM-3 were synthesized on a Fmoc Rink amide solid support resin (Bachem) using Fmoc chemistry on an automated ABI 433 peptide synthesizer (ABD, Perkin Elmer, Foster City, Calif.) according to the manufacturer's standard protocols. Cleavage of the crude product from the resin was carried out in 10 mL of thioanisole:EDT:TFA (1:1:9) for 2 hours at room temperature. Crude cleavage product was precipitated with t-butyl methyl ether, filtered and dried.

1.2 Formation of Disulfide Linkages

The crude linear peptide was dissolved in DMSO and added to 20 mM ammonium acetate, pH 7. The final concentration of peptide was about 1–8 mg/mL, the pH ranged from 7.0–7.2 and the DMSO concentration ranged from about 5–20%. The solution was stirred overnight at room temperature, and the pH of the solution was adjusted to pH 5 with concentrated acetic acid.

The oxidized peptide was loaded onto a preparative reverse-phase HPLC column (Vydac C18, 2.2 cm×25 cm, Cat. No. 218TP101522), the column was washed with buffer (10% v/v acetonitrile, 0.1% v/v TFA in water) until absorbance of the effluent (measured at 235 cm) reached baseline and the pure product was eluted at 10 mL/min. using the following buffers and gradient:

| Time (min.) | Buffer A (%) | Buffer B (%) | Gradient |
|---|---|---|---|
| 0 | 90 | 10 | linear |
| 10 | 82 | 18 | linear |
| 80 | 68 | 32 | linear |
| 95 | 5 | 95 | linear |

Buffer A=0.10% (v/v) aqueous TFA;
Buffer B=0.08% (v/v) TFA in acetonitrile.

Fractions were analyzed by analytical HPLC. Fractions containing the desired disulfide-bridged peptide were pooled, the acetonitrile stripped and the resultant aqueous solution lyophilized to dryness. The sequence of the disulfide-bridged peptide was confirmed by mass spectrometry.

EXAMPLE 2

Preparation of Hydroxypropylmethylcellulose (HPMC) Gel Formulation

This Example provides preferred methods for preparing the preferred topical formulations of the invention.

A topical gel of OM-3 containing the following ingredients was prepared as follows:

| Ingredient | Percent (w/w) |
| --- | --- |
| OM-3 | 1.0 |
| Sorbitol solution (70%) USP | 10.0 |
| Xylitol NF | 3.0 |
| Hydroxypropyl methylcellulose USP | 2.0 |
| Lactic acid USP | 0.1 |
| Methylparaben NF | 0.18 |
| Propylparaben NF | 0.02 |
| Purified Water USP q.s. | 100 |
| 1 N. sodium hydroxide or 1 N hydrochloric acid q.s. | pH4.2 ±0.2 |

Methylparaben and propylparaben were dissolved in hot aqueous lactate buffer solution (pH 4.2). Hydroxypropyl methylcellulose (HPMC) was dispersed in the hot solution followed by addition of sorbitol, xylitol and aqueous OM-3. The mixture was cooled to room temperature, becoming viscous with cooling.

EXAMPLE 3

In Vitro Antimicrobial Assays

This Example describes preferred assays for identifying protegrin peptides useful in the methods of the invention. Unless otherwise indicated, all in vitro assay data reported herein was obtained using the methods described below.

The following equipment, reagents, stock solutions and cultures are used in the assays that follow.

Microorganisms: *Escherichia coli* ML-35p and vancomycin-resistant *Enterococcus faecium* (VREF) were obtained from Dr. Robert Lehrer (UCLA, see also, Lehrer et al., 1988, *J. Immunol. Methods* 108:153) and Dr. Gary Schoolnik (Stanford), respectively. *Pseudomonas aeruginosa* (ATCC 9027), *Candida albicans* (ATCC 1023), methicillin sensitive *S. aureus* (ATCC 19636), *K. pneumoniae* (ATCC 9997), *S. marcesceus* (ATCC 13880), *S. salivarius* (ATCC 31067), and methicillin resistant *Staphylococcus aureus* (ATCC 33591) were obtained from the American Type Culture Collection, Rockville, Md. *P. mirabilis* was an isolated strain obtained from the cheek pouch of a hamster.

Microorganisms from other sources, such as, for example, clinical isolates, can be used interchangeably with the above-described microorganisms in the assays described herein.

Media and Reagents

Trypticase Soy Agar (TSA; Becton-Dickinson, Cockeysville, Md., BBL #4311768): dissolve 40 g in 1 Liter deionized water, autoclave 121° C., 20 minutes.

Trypticase Soy Broth (TSB; Becton-Dickinson, Cockeysville, Md., BBL #4311768): dissolve 30 g in 1 Liter deionized water, autoclave 121° C., 20 minutes, and store at room temperature.

2× Trypticase Soy Broth (2×TSB): dissolve 60 g in 1 Liter deionized water, autoclave 121° C., 20 minutes, and store at room temperature.

Glycerol (20% v/v): mix 20 mL glycerol with 80 mL deionized water, Filter sterilize with $0.20\mu$ filter and store at room temperature.

Monobasic phosphate buffer (100 mM): dissolve 13.7 g sodium phosphate monobasic (Fisher #S368–500) in 1 Liter deionized water. Filter sterilize with $0.20\mu$ filter and store at room temperature.

Dibasic phosphate buffer (100 mM): dissolve 14.2 g sodium phosphate dibasic (Fisher #S374–500) in 1 Liter deionized water. Filter sterilize with $0.45\mu$ filter and store at room temperature.

Phosphate-buffered saline (PBS; 10 mM phosphate, 100 mM NaCl, pH 7.4): mix 15 mL dibasic phosphate buffer (100 mM), 5 mL monobasic phosphate buffer (100 mM), 4 mL NaCl (5 M) and 176 mL deionized water. Adjust pH if necessary, filter sterilize with $0.45\mu$ filter and store at room temperature.

Phosphate buffer (100 mM, pH 6.5): mix 40 mL dibasic phosphate buffer (100 mM) with 160 mL monobasic phosphate buffer (100 mM). Adjust pH if necessary, filter sterilize with $0.45\mu$ filter and store at room temperature.

Liquid Testing Medium (LTM): aseptically combine the following sterile ingredients: 10 mL Phosphate buffer (100 mM, pH 6.5), 1.0 mL TSB, 2 mL NaCl (5 M) and 87 mL deionized water. Store at room temperature.

Acetic acid (0.01% v/v): mix 10 $\mu$L acetic acid with 100 mL sterile deionized water.

Agarose: mix 1 g agarose (Sigma #S6013) in 80 mL deionized water, autoclave 121° C., 20 minutes.

Agarose Underlay Medium: combine 10 mL Phosphate buffer (100 mM, pH 6.5), 1.0 mL TSB, 2 mL NaCl (5 M) and 7 mL deionized water with 80 mL tempered (50° C.) agarose.

2×TSB Agrarose Overlay Medium: dissolve 60 g TSB and 10 g agarose in 1 Liter deionized water, aliquot 100 mL per bottle, autoclave 121° C., 20 minutes, and store at room temperature.

Preparation of Microorganism Slants: Each strain was cultured on TSA. Isolated colonies were transferred into TSB (10 mL in a sterile 50 mL Erlenmeyer flask) using a sterile, disposable loop and the flask incubated at 37° C. (bacteria) or 30° C. (yeast) with shaking (200 RPM) for 16–18 hours.

Broth cultures were diluted 1:1 with 20% sterile glycerol and stored as 1.0 mL aliquots at –80° C. For daily inocula, liquid was transferred from a thawed vial using a sterile loop and then spread onto the surface of TSA slants. The screw capped tubes were incubated overnight and stored at 4° C. for up to one month.

Preparation of Inoculum

1. Remove the cap from tube and lightly touch a sterile loop to the area of heavy growth on the TSA slant.
2. Inoculate 10 mL of TSB (50 mL flask) and incubate the flask in a shaking water bath for 18 hours (overnight) at 37° C. (bacteria) or 30° C. (yeast) at 200 RPM.
3. In a cuvette, dilute 50 $\mu$L of the overnight culture 1:20 with TSB and measure the absorbance at 600 nm ($A_{600}$) using TSB as a reference. The $A_{600}$ of the diluted culture should be between 0.1–0.4.
4. In a 250 mL Erlenmeyer flask, dilute 50 $\mu$L of the overnight culture 1:1000 with TSB (bacteria) or 1:100 with TSB (yeast).
5. Incubate the flask in a shaking water bath at 37° C. (bacteria) or 30° C. (yeast) at 200 RPM for approximately 2–3 hours until log-phase is reached, i.e. until the $A_{600}$ of the culture is between 0.200 and 0.400 without further dilution.

6. Transfer 25 mL of the log-phase culture to a sterile centrifuge tube and centrifuge at 2000 rpm and 4° C. for 10 minutes. Decant the supernatant, add 25 mL of sterile PBS and resuspend the pellet by vortexing.

7. Centrifuge the suspension at 2000 rpm and 4° C. for 10 minutes. Decant the supernatant and resuspend the pellet with 5 ml sterile PBS.

8. Measure the $A_{600}$ of the undiluted suspension. If the absorbance is above 0.5, dilute with sterile PBS until the absorbance is between 0.100 and 0.500.

9. Determine the number colony-forming units per milliliter suspension (CFUs/mL) by preparing 10-fold serial dilutions in saline (0.87%) and spreading 100 μL of the $10^4$-, $10^5$-, and $10^6$-fold dilutions onto TSA plates, one dilution per plate. Incubate overnight, count the number of colonies and determine the CFUs/mL (an accurate determination requires approximately 30–300 colonies per plate).

Preparation of Peptide Stock Solutions

1. Weigh approximately 1.0 mg of each peptide to be tested into a sterile polypropylene cryovial (1.8 mL).
2. Add sufficient acetic acid (0.01%) to make a stock solution having a concentration of 1280 μg/mL. Dispense the stock solution into several vials, 100 μL per vial, and store the aliquots, tightly sealed, at −80° C.

3.1 Radial Diffusion (MCZ) Assay

The MCZ assay uses minimal amounts of test materials to determine the sensitivity of microorganisms to various antimicrobial compounds. Cells are grown to approximately mid-log phase and resuspended in minimal nutrient buffered agarose. Agarose (not agar) is used in this gel to avoid electrostatic interactions between antimicrobial peptides and the polyanionic components of standard agar. Peptides diffuse radially into the gels from small wells and the diameter of the zone of growth inhibition is proportional to the concentration of peptide in the solution (Lehrer et al., 1988, J. Immunol. Methods 108:153).

Preparation of MCZ Assay Plates

1. For each petri plate to be poured, dispense 10 mL of tempered (50° C.) Agarose Underlay Medium into a sterile polypropylene tube (15 mL). Add $4 \times 10^6$ CFUs of the desired strain to each tube. Mix well by inverting tube 3 times. Immediately pour the molten agarose into the petri dishes.
2. After the agarose has solidified, use a sterile canula (3 mm i.d.) to punch 16 wells (4×4 evenly spaced grid) into the agarose. Remove the agarose plugs with a pasteur pipette and trap the agarose in a flask with a side arm port attached to a vacuum.
3. From the peptide stock solution, prepare serial 2-fold dilutions (from 128 μg/mL to 0.06 μg/mL) using acetic acid (0.01%) as a diluent, or, for peptide concentrations lower than 50 μg/mL, sodium acetate (10 mM, pH 5) containing Human Serum Albumin (HSA; 0.1% w/v) as a diluent.
4. Dispense 5 μL of each serial dilution into the agarose wells, one serial dilution per well.
5. Dispense diluents into wells as negative controls and protegrin-1 (U.S. Pat. No. 5,464,823; 32 μg/mL, 8 μg/mL and 2 μg/mL) into wells as positive controls.
6. Incubate the plates at 37° C. (bacteria) or 30° C. (yeast) for 3 hours.
7. Dispense 2×TSB Agarose Overlay Medium (10 mL) onto the surface of each plate, allow the agar to solidify and incubate plates, inverted, at 37° C. (bacteria) or 30° C. (yeast) for 16–18 hours.
8. Examine the plates and measure (in mm) the diameter of the zone of growth inhibition (area of clearing around each well).
9. Plot the diameter of the zone of growth inhibition (Y-axis) versus the concentration of peptide in the well (X-axis) and obtain the line of best fit using linear regression analysis. The X-intercept of the line of best fit is the minimum concentration for zone of growth inhibition (MCZ) for each peptide concentration.

3.2 Microbroth Dilution (MCB) Assay

The microbroth dilution method accommodates large numbers of samples and is more amenable to automation than the MCZ assay and the data analysis is direct and simple. A key step in this assay is combining microorganisms and peptide in a defined minimal nutrient buffer system that minimizes interference with the peptide's biological activity. In addition, the presence of 0.1% (w/v) human serum albumin (HSA) to the peptide diluent minimizes adsorption of peptide to the container.

Preparation of MCB Assay Plates

1. Dispense 100 μL of log-phase cells in LTM ($4 \times 10^5$ CFUs/mL) into each well of a sterile 96-well microtiter plate.
2. From the peptide stock solution, prepare serial two-fold dilutions (from 1280 μg/mL to 0.625 μg/mL) using acetic acid (0.01%) as a diluent, or, for peptide concentrations lower than 50 μg/mL, sodium acetate (10 mM, pH 5) containing Human Serum Albumin (HSA; 0.1% w/v) as a diluent.
3. Dispense triplicate aliquots (11 μL) of each serial two-fold dilution into the wells of the microtiter plate.
4. Incubate the plate at 37° C. (bacteria) or 30° C. (yeast) for 3 hours.
5. Add 100 μL of 2×TSB to each well, mix, and incubate at 37° C. (bacteria) or 30° C. (yeast) for an additional 16–18 hours.
6. Examine the plates and evaluate each well for turbidity (cell growth). Often, MRSA will settle out and form a pellet at the bottom of the well. MRSA can be evaluated by placing the microtiter plate on a stand and examining the bottom of the well using a tilted mirror.
7. The minimum concentration for inhibition of growth in broth medium (MCB) is defined as the lowest concentration of peptide that inhibits all visible growth. If the MCB values for each of the triplicate samples differ, the MCB is obtained by averaging the results of the three samples.
8. The minimum concentration of peptide showing 100% biocidal activity is determined by incubating a 10 μL aliquot from each well on a TSA plate for 24 hours at 37° C. (bacteria) or 30° C. (yeast) (for plating, 1.5 mL TSA in each well of a 24-well plate minimizes cross contamination).

3.3 Modified NCCLS Minimum Inhibitory Concentration (MIC) Assay

The National Committee for Clinical Standards (NCCLS) requires that test compounds be prepared as stock solutions in Mueller-Hinton Broth ("MHB") at 512 μg/mL. The stock solutions are serially diluted (two-fold) in medium and each serial dilution added 1:1 to medium containing $1 \times 10^6$ CFU/mL bacteria (National Committee on Clinical Laboratory Standards, December 1994, "Performance Standards for Antimicrobial Susceptibility Testing," *NCCLS Document M100-S5* Vol. 14, No. 16; *Methods for Dilution Antimicrobial Susceptibility Test for Bacteria that Grow Aerobically,* 3d Ed., Approved Standard M7-A3, National Committee for Clinical Standards, Villanova, Pa.).

It has been found that protegrin peptides precipitate in MHB at concentrations greater than 128 µg/mL. Thus, following the NCCLS protocol would result in serial two-fold dilutions containing less peptide than calculated, yielding erroneously high MIC values.

To overcome this problem, the following modified NCCLS assay is the preferred method for determining MICs of protegrin peptides. In the method, precipitation is avoided by preparing concentrated (10x) stock solutions of test peptide in a buffer that is suitable for the peptide and which does not exhibit deleterious effects on the microorganisms (0.01% v/v acetic acid, 0.1% w/v HSA) and diluting the stock 1:10 into MHB containing the microorganisms.

Preparation of MIC Assay Plates
1. Prepare a fresh overnight culture of test organism in Meuller-Hinton broth (MHB; Becton-Dickinson, Cockysville, Md., BB2 #11443).
2. Dilute the culture to approximately $4 \times 10^5$ CFUs/mL with fresh MHB and dispense 100 µL aliquots into each well of a sterile 96-well microtiter plate.
3. From the peptide stock solution, prepare serial two-fold dilutions (from 1280 µg/mL to 0.625 µg/mL) using acetic acid (0.01%) as a diluent, or, for peptide concentrations lower than 50 µg/mL, sodium acetate (10 mM, pH 5) containing Human Serum Albumin (HSA) or bovine serum albumin (BSA) (0.1%–0.2% w/v) as a diluent.
4. Dispense triplicate aliquots (11 µL) of each serial dilution into the wells of the microtiter plate.
5. Incubate the plate for 16–18 hours, without aeration, at 37° C. (bacteria) or 30° C. (yeast).
6. Examine the plates and evaluate each well for turbidity (cell growth). Often, MRSA will settle out and form a pellet at the bottom of the well. MRSA can be evaluated by placing the microtiter plate on a stand and examining the bottom of the well using a tilted mirror.
7. The minimum inhibitory concentration (MIC) is defined as the lowest peptide concentration that inhibits all visible growth. If the MIC values for each of the triplicate samples differ, the MIC is obtained by averaging the results of the three samples.
8. The minimum concentration of peptide showing 100% biocidal activity is determined by incubating a 10 µL aliquot from each well on a TSA plate for 24 hours at 37° C. (bacteria) or 30° C. (yeast) (for plating, 1.5 mL TSA in each well of a 24-well plate minimizes cross contamination).

3.4 Kinetic Bactericidal Assay

The following assay is used to determine the rate at which a protegrin peptide kills a target microorganism, as well as to determine if a particular peptide is bactericidal or bacteriostatic.

Assay Protocol
1. Dispense 200 µL of log-phase cells in LTM ($4 \times 10^5$ CFUs/mL) into each well of a 96-well microtiter plate solution.
2. At time T=0 minutes, add 22 µL of 1280 µg/mL peptide to well A1 and mix by triturating 3 times.
3. Wait 30 seconds and add 22 µL of a second concentration of peptide the to the next well (A2) and mix by triturating 3 times.
4. Repeat the process, staggering each peptide addition by 30 seconds, until all concentrations of peptide have been added. Typically, 4-fold serial dilutions of stock peptide (i.e., 1280, 320, 80, 20 and 5 µg/mL peptide diluted 1:10 into each well) produces good comparative kill curves. Add 22 µL of 0.01% acetic acid to one well as a control.
5. At time T=15 minutes, mix well A1 by triturating 3 times and transfer 20 µL to an empty sterile petri dish (100 mm×15 mm).
6. Quickly add 20 mL of tempered (50° C.) TSA and gently swirl plate to mix.
7. Repeat steps 5–6 until all peptide concentrations have been plated.
8. For the control well, dilute the sample 1:100 with LTM and plate 50 µL of the dilution to obtain an accurate determinations of CFUs.
9. After the agar has solidified, invert the plates and incubate at 37° C. (bacteria) 30° C. (yeast) for 18–24 hours.
10. Repeat steps 5–9 for all peptide concentrations and control samples at times T=30, 60, 120, and 240 minutes.
11. Count the number of CFUs per plate and estimate the reduction in CFUs for each peptide concentration. In order to assess an effect using this assay, the peptide must reduce the CFUs by at least one log (i.e., at least 800 CFUs per plate). Although such numbers are higher than recommended for accuracy (30–300 CFUs/plate), log-order changes in recoverable CFUs indicate significant bacteriocidal efficacy.
12. To obtain comparative kill curves, plot the log of fractional survival versus peptide concentration.

EXAMPLE 4

In Vitro Antimicrobial Activity of PG-1 (SEQ ID NO:1)

The antimicrobial activity of PG-1 (as well as other protegrins) is described in WO 95/03325 (published Feb. 2, 1995). Briefly, PG-1 exhibits broad spectrum anti-microbial activity, being extremely effective against *L. monocytogenes,* strain EGD, *C. albicans, S. aureus, K. pneumoniae* 270, *P. aeruginosa, S. typhimurium, H. capsulatum, Mycobacterium avium-intracellulare* and *Mycobacterium tuberculosis.* Antimicrobial activity is observed in the presence of 90% fetal calf serum.

EXAMPLE 5

In Vitro Antimicrobial Activity of OM-3 (SEQ ID NO:3) Against Pathogens Associated With Oral Mucositis This Example demonstrates the antimicrobial activity of the native form of preferred peptide OM-3 against pathogen associated with oral mucositis. Although more than 200 species of microorganisms have been isolated from the oropharynx, individual surfaces of the oral cavity are dominated by specific subgroups (Liljemark et al., 1994, In: *Oral Microbiology and Immunology,* pp. 120–128, Nisengard and Newman, Eds., Saunders Co., Philadelphia). In the saliva and buccal mucosa, alpha and non-hemolytic streptococci are most prevalent (Loeshe, 1994, In: *Oral Microbiology and Immunology,* pp. 307–315, Nisengard and Newman, Eds., Saunders Co., Philadelphia). *S. salivarius,* a representative species of this group, was tested in the radial diffusion assay described above (except that fetal calf serum was added to the overlay at 10%) to determine susceptibility to peptide OM-3.

While Gram-positive bacteria are the most common flora in the oral cavity, lower levels of Gram-negative bacteria and fungi are also present. To determine the efficacy of OM-3 against a wider range of potential pathogens, the MICs (with and without HSA or BSA) of the peptide against a variety of pathogens, including methicillin sensitive and resistant *Staphylococcus aureus* (MSSA, MRSA, respectively), vancomycin resistant *E. faecium* (VREF), *P. aeruginosa, E. coli, K. pneumoniae, Serratia marcescens, Proteus mirabilis,* and *C. albicans* was determined using the modified NCCLS method described above.

5.1 Results

Linear regression analysis of the zone of growth inhibition of *S. salivarius* plotted against OM-3 concentration indicated that the minimum concentration for inhibition of growth (MCZ) for OM-3 is 0.38 μg/ml.

The MICs obtained for OM-3 are provided in Tables 4 and 5, below. In Table 4, the MIC values represent the average of three determinations of the concentration in the first well with no growth. In Table 5, the data represents the average of three determinations for each individual strain tested. In general, the MIC values obtained for each organism were equal to the minimum bactericidal concentration (MBC) observed for the same organism (data not shown).

TABLE 4

Minimum Inhibitory Concentrations (MIC) of OM-3 With HSA or BSA

| Microorganism | MIC (μg/ml) |
|---|---|
| MSSA | 1 |
| MRSA | 4 |
| VREF | 0.25 |
| *P. aeruginosa* | 1.3 |
| *E. coli* | 0.25 |
| *K. pneumoniae* | 1 |
| *S. marcescens* | 16 |
| *P. mirabilis* | 128 |
| *C. albicans* | 8 |

TABLE 5

Minimum Inhibitory Concentrations CMIC) of OM-3

| Assay Medium | Organism Type | Genus-species | No. Strains | MIC (μg/mL) Low | MIC (μg/mL) High |
|---|---|---|---|---|---|
| Mueller Hinton Broth | Gram-positive | *Enterococcus faecalis* VSE | 1 | 2 | |
| | | *Enterococcus faecalis* VSE | 2 | 2 | 4 |
| | | *Enterococcus faecium* VRE | 3 | 0.25 | 0.5 |
| | | *Staphylococcus aureus* MSSA | 16 | 1 | 4 |
| | | *Staphylococcus aureus* MRSA | 3 | 1 | 2 |
| | | *Staphylococcus epidermidis* MSSE | 14 | 0.13 | 0.8 |
| | | *Staphylococcus epidermidis* MRSE | 2 | 1 | |
| | | *Staphylococcus salivarius* | 2 | 0.2 | 1 |
| | Gram-negative | *Acinetobacter calcoaceticus* | 4 | 0.06 | 2 |
| | | *Escherichia coli* | 5 | 0.25 | 1 |
| | | *Klebsiella pneumoniae* | 4 | 1 | 5 |
| | | *Pseudomonas aeruginosa* | 18 | 1 | 8 |
| | | *Serratia marcescens* | 16 | 16 | >256 |
| Mueller Hinton Broth with 2% Lysed horse blood* | Gram-positive | *Corynebacterium minutissimum* | 1 | 0.25 | |
| | | *Corynebacterium pseudodiptheriae* | 1 | 0.25 | |
| | | *Corynebacterium striatum* | 1 | 0.25 | |
| | | *Corynebacterium* group G1 | 1 | 0.25 | |
| | | *Corynebacterius* group G2 | 16 | 1.3 | 16 |
| | | *Streptococcus pneumoniae* | 2 | 16 | 27 |
| | | *Streptococcus mitis*(10 to test) | 14 | 4 | 64 |
| | | *Streptococcus sanguis* | | | |
| | Gram-negative | *Haemophilus influenza* | 15 | 1 | 8 |
| | | *Moraxella sp.* | 12 | 0.2 | 0.8 |
| | | *Neisseria meningitidis* | 1 | 8 | |
| Mueller Hinton Broth | | *Candida albicans* | 1 | 8 | |

*MICS in Mueller Hinton Broth containing lysed horse blood are approximately 4–8 times higher due to interference from blood components as determined by MIC for MRSA: 4 in MHB; 16 in MHB + LHB.

EXAMPLE 6

Bactericidal Activity of OM-3 Against Natural Flora in Human Saliva

This Example demonstrates the ability of preferred peptide OM-3 to decrease CFUs of bacteria found in pooled normal human saliva.

6.1 Experimental Protocol

Peptide OM-3 (20 mM sodium acetate, pH 5) or placebo vehicle was mixed 1:1 with saliva. At 1, 2, 4, 8 and 16 minutes after mixing, aliquots were plated onto Trypticase Soy Agar containing 10% fetal bovine serum, and the plates were incubated overnight at 37° C.

6.2 Results

The results of the experiment are presented in FIG. 1. The data clearly demonstrate that OM-3 kills oral microflora within 2 minutes, in a concentration dependent manner. Since saliva contains many negatively charged glycoproteins such as mucin which may bind the peptide (Bansil et al., 1995, *Annu. Rev. Physiol.* 57:635–57), higher concentrations of OM-3 were required for effective reduction of the natural flora than in the experiments described in Example 5. Placebo vehicle, had no effect on CFUs.

EXAMPLE 7

Effect of Saliva on Antimicrobial Activity

This Example demonstrates the effect of saliva on the antimicrobial activity of a variety of protegrin peptides, as measures by radial diffusion and reduction in CFUs.

7.1 Experimental Protocol

For the radial diffusion experiment, the radial diffusion assay of Qu, X-D et al., *Infect Immun* (1996) 6:1240–1245 was used, except that the media in the underlay agar contained phosphate buffer at 10 mM, pH6.5, 100 mM NaCl, 1% TSB, 1% agarose. The media in the overlay contain 10 mM phosphate buffer, pH 6.5, 100 mM NaCl, 2XTSB, 1% agarose. The peptides were diluted from 10× stock made up in 0.01% acetic acid either with 10 mM acetate buffer (pH 5) or with saliva.

For the reduction of CFUs, the initial inoculum contained approximately $4 \times 10^7$ CFUs/mL saliva. Peptides (320 µg/mL) were dissolved in 0.01% acetic acid and added as 1/10 volume to saliva.

7.2 Results

For the radial diffusion assay, the results are given as the minimal concentration required to produce a detectable zone of clearance, or MCZ—i.e., an extrapolated value to the x-axis when the concentration of peptide is plotted against the diameter of the zone. The results of the radial diffuion assay are shown in Table 6; the reduction in CFUs in Table 7. A large number of the peptides tested showed comparable or even improved activity in the presence of saliva. Many of the peptides tested exhibited greater than a two-log reduction in oral CFUs, even at a low concentration of 320 µg/mL (0.032% w/w).

TABLE 6

Effect of Diluent on MCZ (µg/mL) against *E. coli* 004

| Sequence | | | Acetate buffer | Saliva |
|---|---|---|---|---|
| RGGRLCYCRRRFCVCVGR | | (SEQ ID NO: 1) | 0.48 | 1.14 |
| RGGGLCYARGWIAFCVGR | | (SEQ ID NO: 41) | 4.16 | 38.30 |
| RGGGLCYKRGWIKFCVGR | | (SEQ ID NO: 6) | 2.71 | 0.56 |
| RGWGLCYCRPRFCVCVGR | | (SEQ ID NO: 7) | 0.39 | 12.60 |
| RGGRLCYCRRRFCVCVGR* | | (SEQ ID NO: 2) | 0.59 | 1.45 |
| LCYCRRRFCVCF | | (SEQ ID NO: 42) | 4.14 | 6.11 |
| RLCYCRPRFCVCV | | (SEQ ID NO: 43) | 3.36 | 6.83 |
| LCYCRGRFCVCVGR | | (SEQ ID NO: 10) | 2.37 | 5.68 |
| RLCYCRPRFCVCVGR | | (SEQ ID NO: 8) | 1.60 | 6.86 |
| RWRLCYCRPRFCVCV | | (SEQ ID NO: 11) | 1.04 | 39.00 |
| RGWRACYCRPRFCACVGR | | (SEQ ID NO: 13) | 0.71 | 1.84 |
| GWRLCYCRPRFCVCVGR | | (SEQ ID NO: 14) | 0.86 | 47.50 |
| RLCACRGRACVCV | | (SEQ ID NO: 44) | 13.70 | 9.76 |
| WLCYCRRRFCVCV* | | (SEQ ID NO: 16) | 5.05 | 36.00 |
| RLCYCRXRFCVCV | (X = MeGly) | (SEQ ID NO: 17) | 2.43 | 2.54 |
| RLCYCRPRFCVCVGR* | | (SEQ ID NO: 1B) | 3.65 | 12.80 |
| RGGGLCYCRPRFCVCVGR* | | (SEQ ID NO: 19) | 3.51 | 11.90 |
| RRCYCRRRFCVCVGR | | (SEQ ID NO: 25) | 3.02 | 8.07 |

TABLE 7

Log Reduction of CFUs endogenous flora in saliva after 15 minutes exposure to peptide (320 µg/ml)

| Sequence | | | Log reduction CFUs |
|---|---|---|---|
| RGGRLCYCRRRFCVCVGR | | (SEQ ID NO: 1) | 1.80 |
| RGGRLCYCRPRFCVCVGR | | (SEQ ID NO: 5) | 2.04 |
| RGGGLCYKRGWIKFCVGR | | (SEQ ID NO: 6) | 1.09 |
| RGWGLCYCRPRFCVCVGR | | (SEQ ID NO: 7) | 0.53 |
| RLCYCRPRFCVCVGR | | (SEQ ID NO: 8) | 0.53 |
| RGGGLCYTRPRFTVCVGR | | (SEQ ID NO: 9) | 1.05 |
| RGGRLCYCRRRFCVCVGR* | | (SEQ ID NO: 2) | 1.25 |
| LCYCRGRFCVCVGR | | (SEQ ID NO: 10) | 1.02 |
| RWRLCYCRPRFCVCV | | (SEQ ID NO: 11) | 0.22 |
| RGWRLCYCRPRFCVCVGR | | (SEQ ID NO: 12) | 0.38 |
| RGWRACYCRPRFCACVGR | | (SEQ ID NO: 13) | 0.28 |
| GWRLCYCRPRFCVCVGR | | (SEQ ID NO: 14) | 0.26 |
| XCYCRRRFCVCV | (X = Cha) | (SEQ ID NO: 1S) | 0.25 |

TABLE 7-continued

Log Reduction of CFUs endogenous flora in saliva
after 15 minutes exposure to peptide (320 µg/ml)

| Sequence | | | Log reduction CFUs |
|---|---|---|---|
| WLCYCRRRFCVCV* | | (SEQ ID NO: 16) | 0.16 |
| RLCYCRXRFCVCV | (X = MeGly) | (SEQ ID NO: 17) | 3.43 |
| RLCYCRPRFCVCVGR* | | (SEQ ID NO: 18) | 0.66 |
| RGGGLCYCRPRFCVCVGR* | | (SEQ ID NO: 19) | 1.51 |
| RXCFCRPRFCVCV | (X = Cha) | (SEQ ID NO: 20) | 0.71 |
| RWCFCRPRFCVCV | | (SEQ ID NO: 21) | 0.52 |
| LCXCRRRXCVCV | (X = Cha) | (SEQ ID NO: 22) | 0.23 |
| RGGRLCYCRRRFCVC | | (SEQ ID NO: 23) | 0.86 |
| LCYTRRRFTVCV | | (SEQ ID NO: 24) | 0.64 |
| RRCYCRRRFCVCVGR | | (SEQ ID NO: 25) | 0.98 |
| RLCYCRRRFCVCV* | | (SEQ ID NO: 26) | 0.21 |
| RXRLCYCRZRFCVCV | (X = Cha) (Z = MeGly) | (SEQ ID NO: 27) | <0.6 |
| RGWRLCYCRGRXCVCV | (X = Cha) | (SEQ ID NO: 28) | <0.6 |
| RGLRXCYCRGRFCVCVGR | (X = Cha) | (SEQ ID NO: 29) | 1.6S |
| RGWRGCYKRGRFKGCVGR | | (SEQ ID NO: 30) | <0.97 |
| RGWRGCYCRXRFCGC | (X = MeGly) | (SEQ ID NO: 31) | <0.6 |
| RGGLCYCRGRFCVCVGR | | (SEQ ID NO: 32) | 2.52 |
| RLLRLCYCRXRFCVCVGR | (X = MeGly) | (SEQ ID NO: 33) | 0.65 |
| RLLRACYCRRFCVCVGR | (X = MeGly) | (SEQ ID NO: 4) | 2.11 |
| RGGRLCYCRGRFCVCVGR* | | (SEQ ID NO: 34) | 2.16 |
| RGWRLCYCRGRFCVCVGR | | (SEQ ID NO: 35) | 1.89 |
| RGGRLCYCRGRFCVCVGR | | (SEQ ID NO: 36) | 2.53 |
| RGGRVCYCRGRFCVCVGR | | (SEQ ID NO: 37) | 2.37 |
| RGGRVCYCRGRFCVCV | | (SEQ ID NO: 38) | 2.07 |
| RGGRVCYCRGRFCVCV* | | (SEQ ID NO: 39) | <0.97 |
| WLCYCRRRFCVCV | | (SEQ ID NO: 40) | 1.87 |

EXAMPLE 8

Effect of Amidated OM-3 (SEQ ID NO:3) on Reducing Oral Microflora in Hamsters

This Example demonstrates the efficacy of preferred peptide OM-3 (SEQ ID NO:3) in reducing the CFUs of natural oral microflora in the cheek pouches of hamsters.

8.1 Experimental Protocol

Peptide OM-3 (SEQ ID NO:3) (1 mg/ml or 5 mg/ml in an aqueous formulation containing hydroxypropylmethylcellulose) was delivered to one cheek pouch of hamsters in a volume of 0.25 ml three times per day for 4 days. Dose groups consisted of 4 hamsters each. Beginning on the second day of dosing, the cheek pouches were swabbed approximately 4 or 15 hours after treatment. The swabs were placed in culture tubes containing 1 mL of 0.87% (w/v) NaCl and 0.1% (w/v) Tween-80 and refrigerated. All culture tubes were mixed virorously within 24 hours of sample collection. After mixing, a 0.1 mL aliquot of undiluted sample and 0.1 mL aliquots of two 100-fold serial dilutions were spread onto standard blood agar plates. Following incubation at 37° C. for at least 24 hours, the number of CFUs per plate was determined.

8.2 Results

Figure 2:
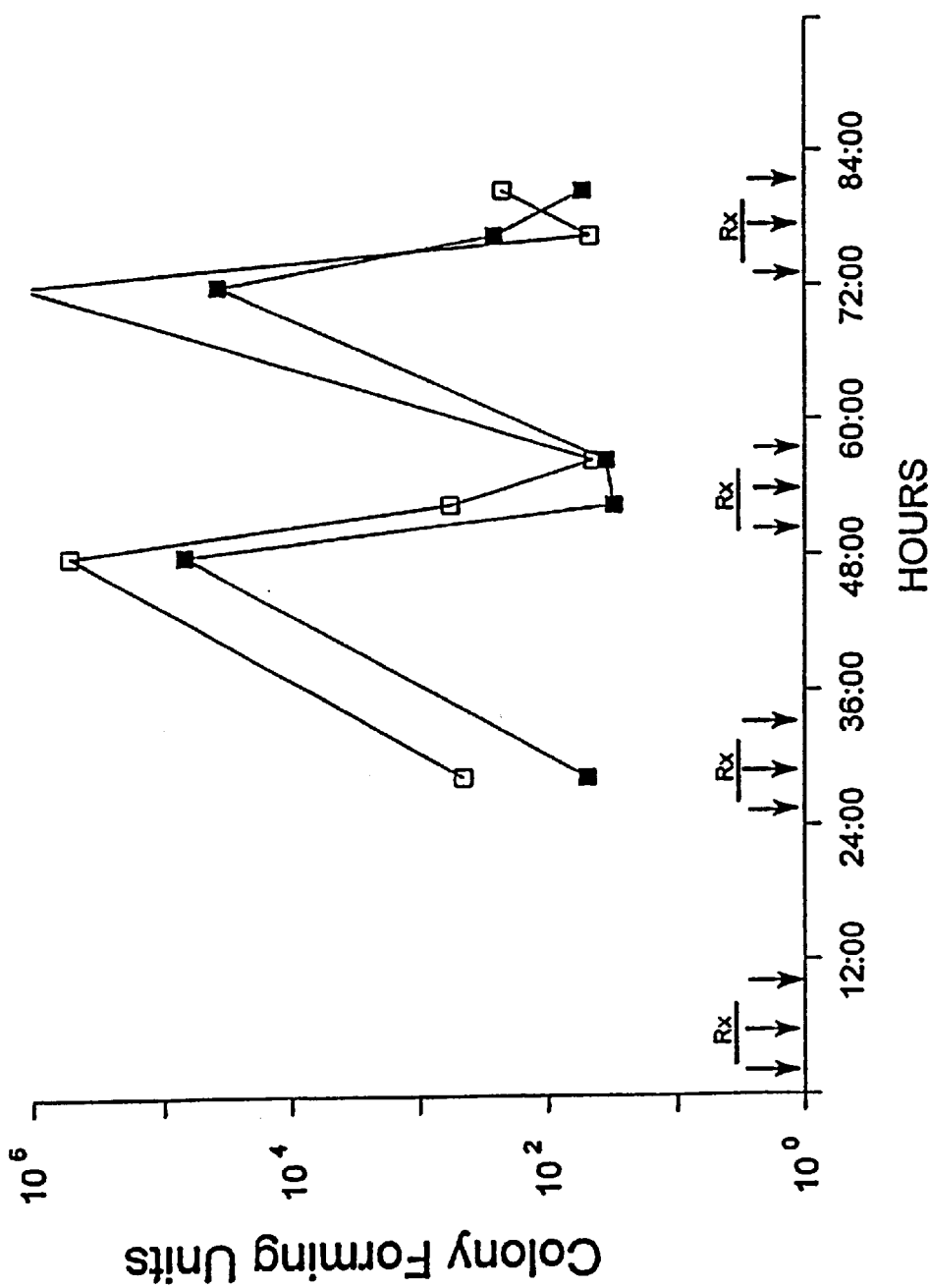
FIG. 2 is a graphical representation of the effect of peptide OM-3 (SEQ ID NO:3) on reduction of oral flora in hamsters.

The results of the experiment are presented in FIG. 2. In FIG. 2, open squares represent treatment with 1 mg/mL peptide; filled squares treatment with 5 mg/mL. The arrows on the X-axis labelled "Rx" indicate the times at which the peptide was applied.

Historically, the number of CFUs in untreated hamsters is generally between $10^6$ and $10^7$ per swab. Compared to historic control values, a 1,000 to 10,000-fold (3–4 log) reduction in oral CFUs was consistently present 4 hours after OM-3 (SEQ ID NO:3) was applied. An expected regrowth of oral flora occurred by 15 hours after treatment. Comparable results were obtained with PG-1 (OM-1; SEQ ID NO:1).

EXAMPLE 9

Effect of PG-1 (OM-1; SEQ ID NO:1) On Oral Mucositis in Hamsters

A hamster model for testing therapies effective against oral mucositis has been developed by Sonis et al. (Sonis et al., 1990, Oral Surg. Oral Med. Oral Pathol. 69:437–443; Sonis et al., 1995, Oral Oncol. Eur. J. Cancer 31B:261–266). In this model, lesions of the oral mucosa are generated by treating the animal with the chemotherapeutic agent, 5-fluorouracil (5-FU), followed by mechanical abrasion of the cheek pouch. The appearance and time course of the resulting lesions in the hamster oral mucosa closely resemble those seen in the human clinical situation. This experiment demonstrates the ability of native PG-1 to reduce the severity of oral mucositis in this model.

9.1 Experimental Protocol

Thirty male hamsters were administered 60 mg/kg of 5-FU intraperitoneally on days 1 and 3 followed by superficial abrasion of the left cheek pouch on day 5. The hamsters were subsequently randomized into two groups, and beginning on day 6, were treated by direct application of 0.5 ml placebo vehicle (2% methocel K4M, 10% propylene glycol, 10% glycerol, 10 mM acetate buffer) or PG-1 (SEQ ID NO:1) formulation (2 mg/ml in the same vehicle) to the mucosa of the left cheek, 6 times per day for 11 days. Mucositis scores were determined by grading coded photographs of the hamster cheek pouch using a standardized 10-point severity scale (Sonis et al., 1995, supra)

9.2 Results

Figure 3:
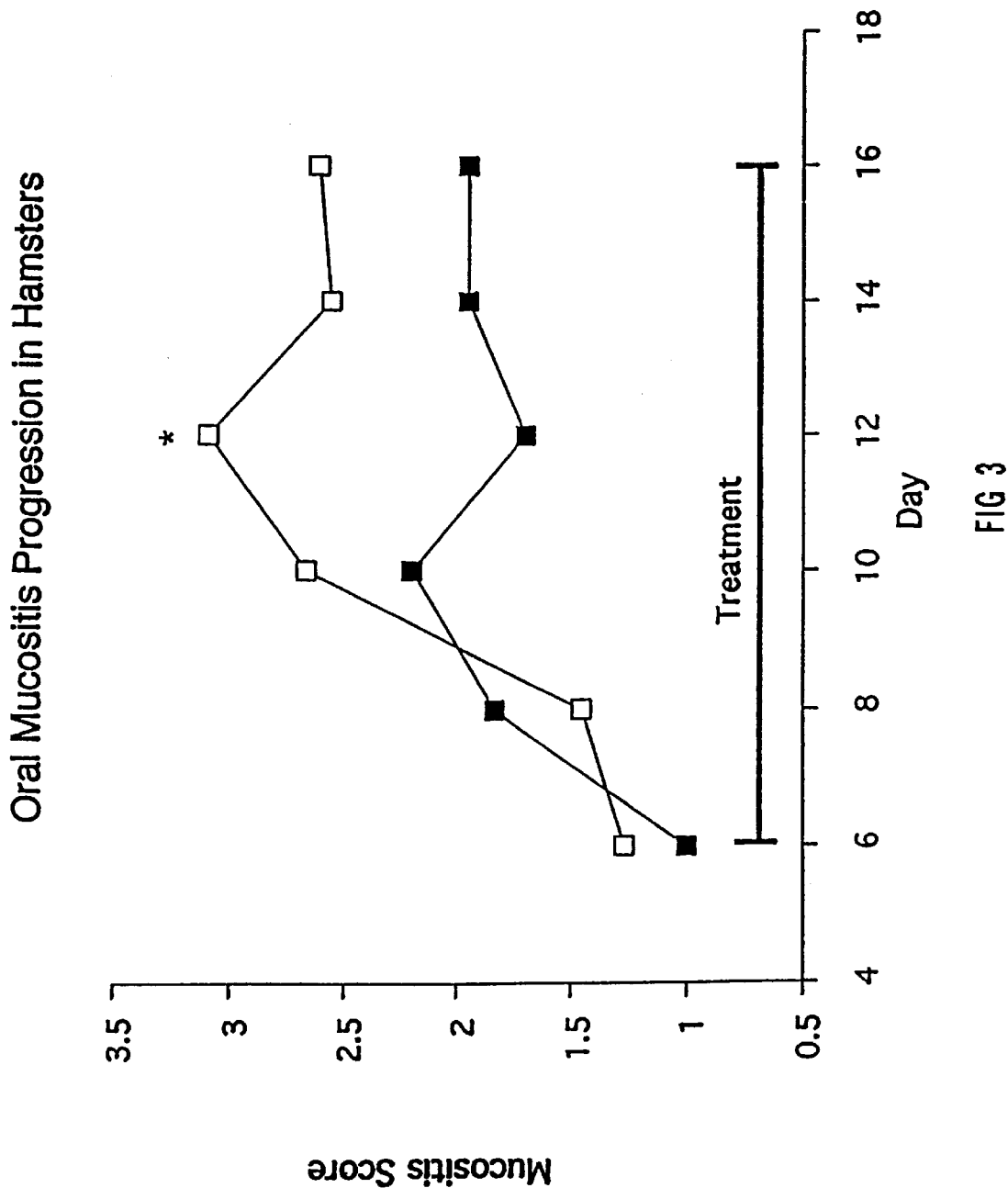
FIG. 3 is a graphical representation of the effect of peptide PG-1 (SEQ ID NO:1) treatment on oral mucositis in hamsters.
Figure 4:
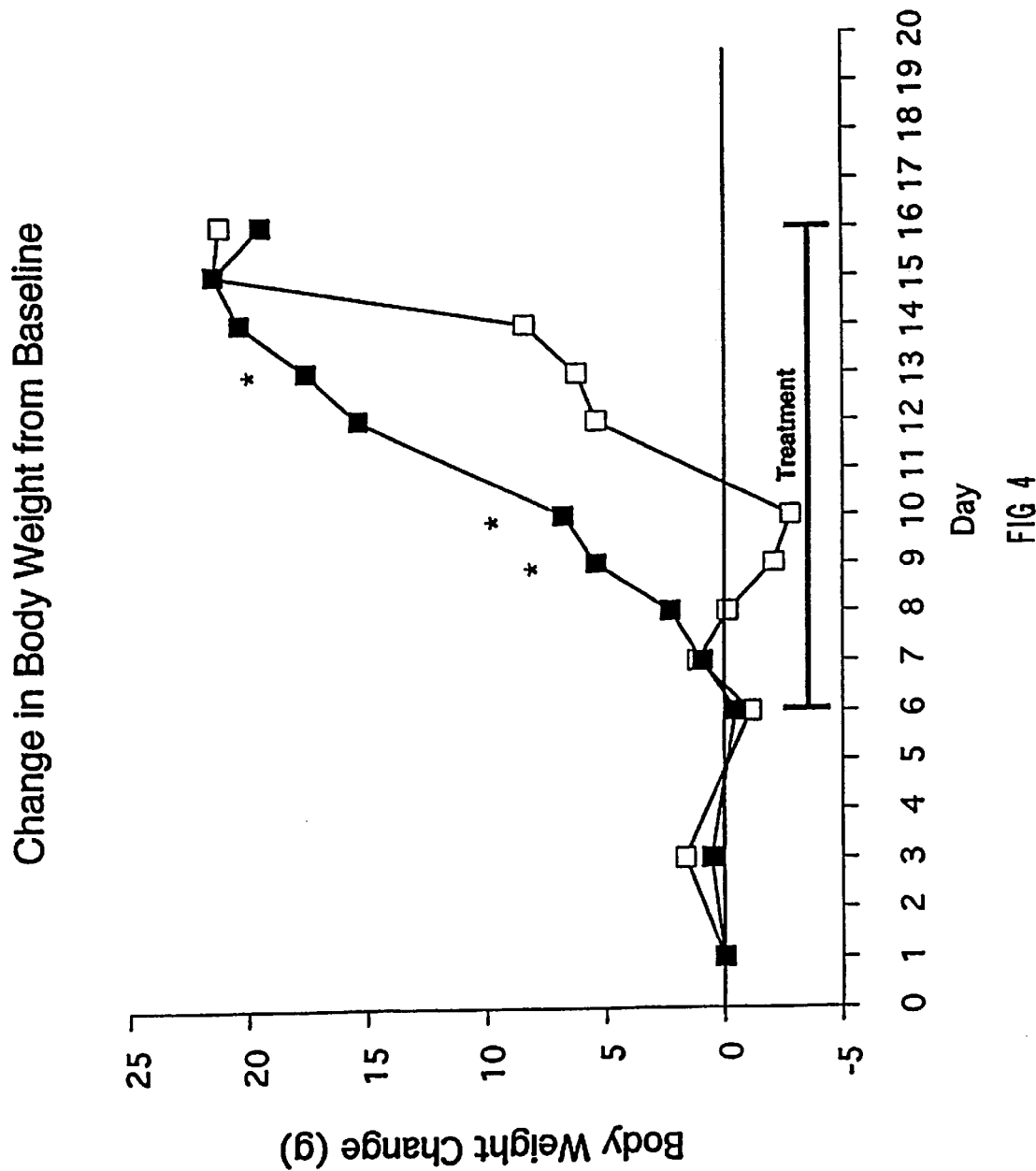
FIG. 4 is a graphical representation of the effect of peptide PG-1 (SEQ ID NO:1) treatment on the body weight of hamsters with experimentally-induced oral mucositis.

The results of the experiment are presented in FIGS. 3 and 4; oral mucositis scores are presented in FIG. 3; percent change in body weight in FIG. 4. In FIGS. 3 and 4, open squares designate treatment with placebo vehicle; closed squares treatment with PG-1 (OM1; SEQ ID NO:1). The asterisks in the FIGS. indicates statistical significance (p<0.05).

As can be seen in FIG. 3, peak severity of mucositis was diminished in the group treated with PG-1 (OM-1; SEQ ID NO:1). In addition, PG-1 (OM-1; SEQ ID NO:1) treatment allowed the animals to gain weight normally, as opposed to the control animals which lost weight, presumably as a result of the severe oral lesions inhibiting food intake (FIG. 4).

The number of CFUs obtained after 2, 6 and 10 days of treatment are presented in Table 8, below. Oral cultures collected after 2, 6 and 10 days of treatment with PG-1 (OM-1; SEQ ID NO:1) showed at least a 100-fold reduction (2 $\log_{10}$) in oral flora CFUs relative to the vehicle controls. This study with PG-1 demonstrates a correlation between reduction in oral CFUs and clinical benefit.

TABLE 8

Reduction In Oral Colony Forming Units (CFUs)

| Treatment Day | Vehicle CFUs | PG-1 CFUs | $\log_{10}$ Reduction In CFUs |
|---|---|---|---|
| 2 | $9.33 \times 10^5$ | $8.9 \times 10^3$ | 2.02 |
| 6 | $6.457 \times 10^6$ | $2.9 \times 10^4$ | 2.33 |
| 10 | $4.786 \times 10^6$ | $3.2 \times 10^4$ | 2.18 |

EXAMPLE 10

Effect of OM-3 (SEQ ID NO:3) Oral Mucositis in Hamsters

This Example demonstrates the ability of OM-3 (SEQ ID NO:3) to reduce the severity of oral mucositis in the hamster pre-clinical model.

10.1 Experimental Protocol

The progression of oral mucositis in the cheek pouch of hamsters was evaluated following topical application of placebo vehicle or OM-3 (SEQ ID NO: 3) formulation. Chlorhexidine gluconate, an agent that has been used to treat oral mucositis, was administered for purposes of comparison.

Male golden Syrian hamsters were randomly assigned to 4 treatment groups consisting of 20 animals each. Mucositis was induced by dosing the hamsters intraperitoneally with 80 mg/kg of 5-FU on days 1 and 4 followed by superficial irritation of the mucosa on day 5. The hamsters were administered 0.5 ml of test formulation by topical application to the left cheek pouch six times per day from day 5 through day 10 and five times on day 11. The test formulations were placebo HPMC gel (group 1; vehicle controls), HPMC gel with 0.5 or 2.0 mg/ml of OM-3 (SEQ ID NO:3) (groups 3 and 4, respectively), or 1.2 mg/ml chlorhexidine gluconate (group 2). OM-3 (SEQ ID NO:3) doses were 0.25 and 1.0 mg/application; the dose of chlorhexidine was 0.6 mg/application. The left cheek pouch of each hamster was everted and photographed on days 6, 8, 10, 11, 12, 13, and 15. At the conclusion of the observation period, the photographs were coded and evaluated independently under code by three trained observers. Body weights were record daily from day 5 through day 18. Oral culture samples were obtained on the third and seventh days of treatment by swabbing the left cheek pouch of 5 hamsters per group with a cotton-tipped applicator. CFUs were determined by suspending the cultures in physiologic saline and plating the suspensions onto standard blood agar plates. Surviving hamsters were euthanized on day 18.

10.2 Results

Figure 5:
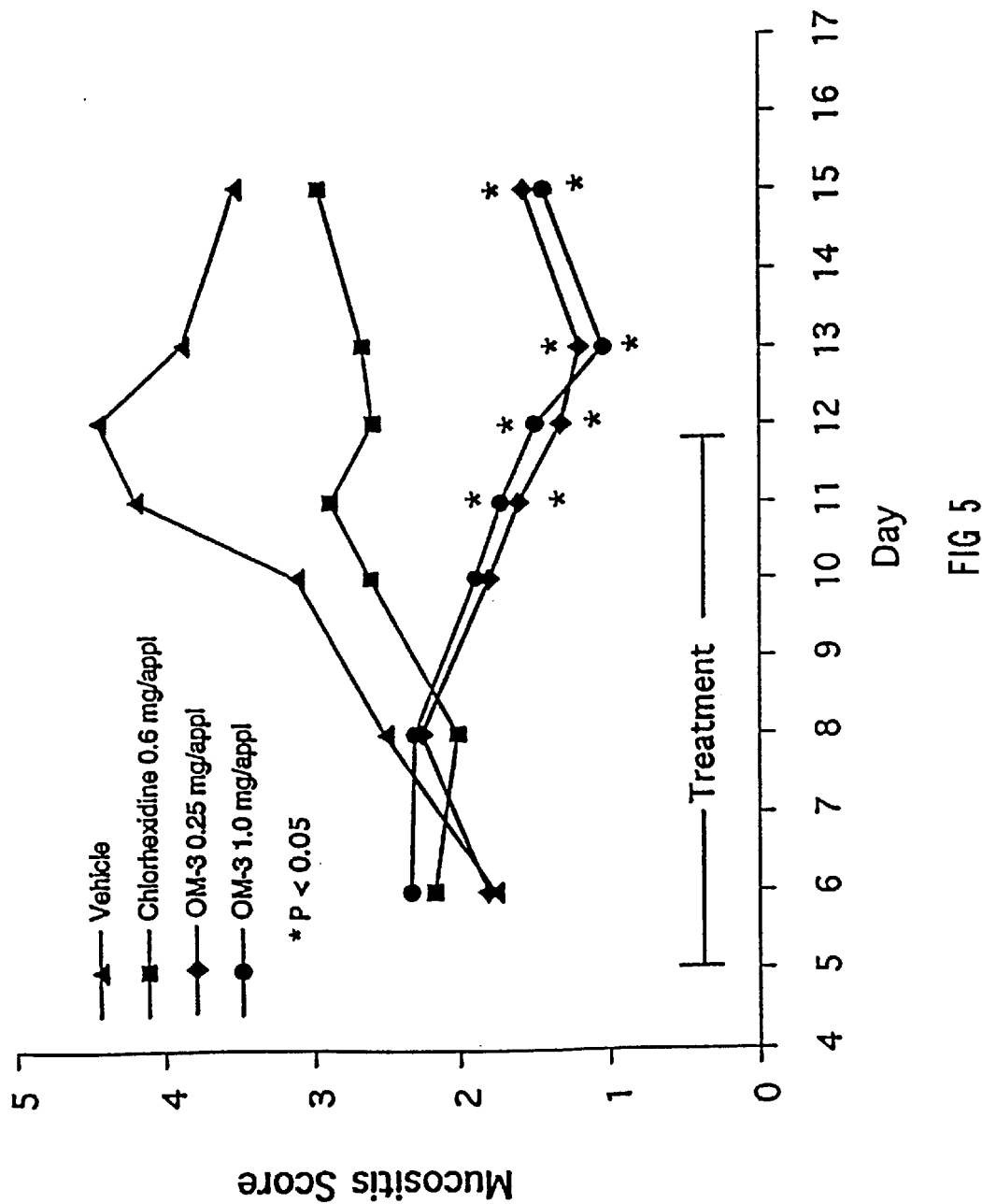
FIG. 5 is a graphical representation of the effect of peptide OM-3 (SEQ ID NO:3) treatment on oral mucositis in hamsters.
Figure 6:
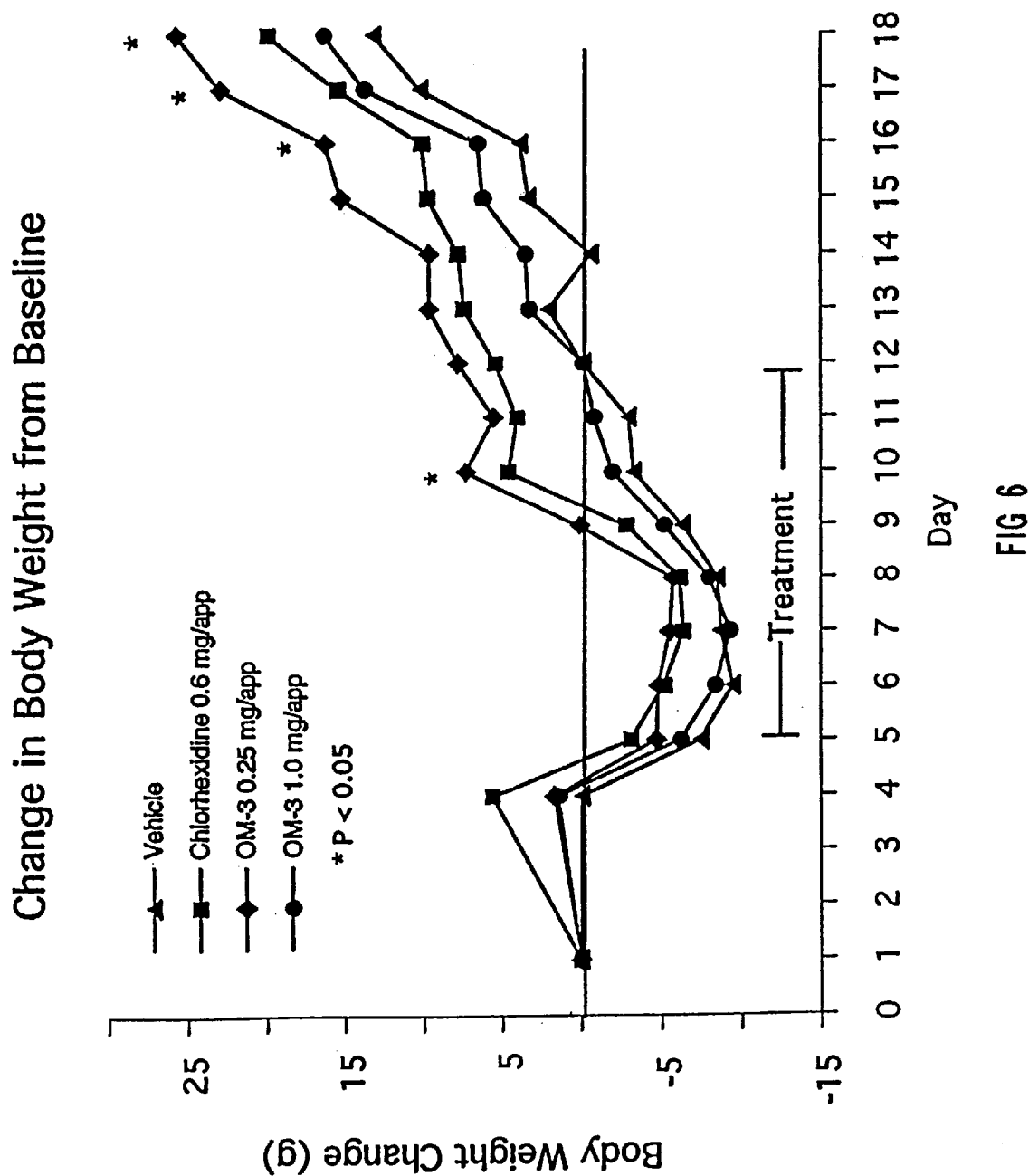
FIG. 6 is a graphical representation of the effect of peptide OM-3 (SEQ ID NO:3) treatment on the body weight of hamsters with experimentally-induced oral mucositis.

The results of the experiments are presented in FIGS. 5 and 6. FIG. 5 is a graphical representation of the progression of oral mucositis in each of the four treatment groups; FIG. 6 is a graphical representation of the change in body weight of each of the four treatment groups. In both FIG. 6 and FIG. 7 triangles represent treatment with placebo vehicle; squares with chlorhexidine, diamonds with 0.25 mg/application OM-3 (SEQ ID NO:3) and circles 1.0 mg/application OM-3). Asterisks represent statistical significance (p<0.05). CFUs determined on the third and seventh day of treatment for each of the four groups are presented in Table 9, below.

TABLE 9

ORAL CFUs IN HAMSTERS WITH ORAL MUCOSITIS

| Treatment | Treatment Day 3 (avg. CFUs/swab) | Treatment Day 7 (avg. CFUs/swab) |
|---|---|---|
| Vehicle | $4.07 \times 10^6$ | $8.85 \times 10^5$ |
| Chlorhexidine | $2.48 \times 10^3$ | $6.32 \times 10^4$ |
| ON-3 (0.25 mg) | $7.29 \times 10^3$ | $3.78 \times 10^3$ |
| OM-3 (1.0 mg) | $3.37 \times 10^2$ | $4.76 \times 10^2$ |

Beginning on study day 11 and continuing through the last day of observation (day 15), mucositis scores were significantly lower (p<0.05) in hamsters treated with OM-3 (SEQ ID NO:3) when compared to the vehicle-treated controls. There was no apparent difference in averaged scores between animals given 0.25 or 1.0 mg of OM-3 (SEQ ID NO:3) per application (0.5 and 2.0 mg/ml, respectively). Among hamsters administered chlorhexidine, mucositis scores tended to be lower than in the vehicle controls on days 11, 12 and 13; however, none of the differences were statistically significant. The mean body weight gain of hamsters receiving 0.25 mg of OM-3 (SEQ ID NO:3) per application tended to be higher than that of the vehicle controls during the interval from day 9 to day 18. The differences were statistically significant on days 10, 16, 17, and 18.

Oral CFUs in animals receiving OM-3 (SEQ ID NO:3) were generally reduced in a concentration-dependent manner. Survival was generally comparable across all treatment groups.

EXAMPLE 11

Dose-Response of OM-3 (SEQ ID NO:3) Against Oral Mucositis in Hamsters

This Example demonstrates the dose-response of OM-3 (SEQ ID NO:3) treatment in the hamster pre-clinical oral mucositis model.

11.1 Experimental Protocol

Male golden Syrian hamsters were randomly assigned to 4 treatment groups consisting of 20 animals each. Mucositis was induced by dosing the hamsters intraperitoneally with 5-fluorouracil (5-FU) on days 1 and 3 followed by superficial irritation of the mucosa on days 5 and 6. The hamsters were administered 0.5 ml of test formulation by topical application to the left cheek pouch six times per day from day 5 through day 12. Vehicle and formulations containing 0.12, 0.5, and 2.0 milligrams of OM-3 (SEQ ID NO:3) per milliliter were delivered at doses of 0 (vehicle) 0.06, 0.25 and 1.0 milligrams of OM-3 (SEQ ID NO:3) per application, respectively. The left cheek pouch of each hamster was everted and photographed on day 6, 8, 9, 10, 11, 12, 13, 15 and 17 for assessment of oral mucositis. Body weights were recorded daily from day 5 through day 17. Culture samples obtained 1 and 3 hours after dosing on the fourth and seventh days of treatment were used to determine mucosal levels of bacteria. Surviving hamsters were euthanatized on day 17.

11.2 Results

Treatment of hamsters with OM-3 (SEQ ID NO:3) resulted in a dose-dependent reduction in the severity and duration of oral mucositis. Relative to the vehicle controls, mucositis scores were significantly lower ($p<0.05$) in each OM-3-treated group on day 6, the day after treatment began. Mucositis scores were also significantly lower on day 8 among hamsters receiving 0.25 milligrams of OM-3 (SEQ ID NO:3) per application and were significantly lower on days 8 and 9 in hamsters receiving 1.0 milligram of OM-3 (SEQ ID NO:3) per application. Among hamsters receiving 1.0 milligram of OM-3 (SEQ ID NO:3) per application, body weight gain was significantly greater than the vehicle controls on days 11, 13, 14 and 16. Oral colony forming units (CFUs) in animals receiving 0.06 or 0.25 milligrams of OM-3 (SEQ ID NO:3) per application were reduced in a dose-dependent manner. Comparable reductions in oral CFUs were present among animals in the mid- and high-dose groups. On the fourth day of treatment, mean bacterial counts of the vehicle-control, low-dose, mid-dose, and high-dose groups were the $3.4 \times 10^5$, $9.4 \times 10^2$, $1.6 \times 10^1$, and $2.3 \times 10^1$, respectively, at the 1-hour postdosing time point and were $1.4 \times 10^6$, $6.8 \times 10^3$, $8.8 \times 10^1$, and $3.3 \times 10^1$, respectively, at the 3-hour postdosing time point. Similar OM-3 (SEQ ID NO:3) related reductions in CFUs were present at 1 and 3 hours postdosing on the seventh day of treatment. When compared to the vehicle-control group, survival was generally higher in groups receiving OM-3 (SEQ ID NO:).

The present invention is not to be limited in scope by the exemplified embodiments, which are intended as illustrations of single aspects of the invention. Indeed, various modifications of the invention in addition to those described herein will become apparent to those having skill in the art from the foregoing description and accompanying drawings. Such modifications are intended to fall with in the scope of the appended claims.

All references cited herein are hereby incorporated by reference in their entireties for all purposes.

---

What is claimed is:

1. A method of treating or preventing oral mucositis in a subject, said method comprising the step of topically administering the oral cavity of said subject a therapeutically effective amount of an antimicrobial peptide selected from the group consisting of:

| | | |
|---|---|---|
| (OM-3) RGGLCYCRGRFCVCVGR | (SEQ ID NO:3); | |
| (OM-4) RLLRACYCRXRFCVCVGR (X = MeGly) | (SEQ ID NO:4); | |
| (OM-6) RGGGLCYKRGWIKFCVGR | (SEQ ID NO:6); | |
| (OM-7) RGWGLCYCRPRFCVCVGR | (SEQ ID NO:7); | |
| (OM-8) RLCYCRPRFCVCVGR | (SEQ ID NO:8); | |
| (OM-10) LCYCRGRFCVCVGR | (SEQ ID NO:10); | |
| (OM-11) RWRLCYCRPRFCVCV | (SEQ ID NO:11); | |
| (OM-12) RGWRLCYCRPRFCVCVGR | (SEQ ID NO:12); | |
| (OM-13) RGWRACYCRPRFCACVGR | (SEQ ID NO:13); | |
| (OM-14) GWRLCYCRPRFCVCVGR | (SEQ ID NO:14); | |
| (OM-15) XCYCRRRFCVCV (X = Cha) | (SEQ ID NO:15); | |
| (OM-16) WLXYXRRRFCVCV* | (SEQ ID NO:16); | |

```
                -continued
(OM-17)
RLCYCRXRFCVCV (X = MeGly)      (SEQ ID NO:17);

(OM-18)
RLCYCRPRFCVCVGR*               (SEQ ID NO:18);

(OM-20)
RXCFCRPRFCVCV (X = Cha)        (SEQ ID NO:20);

(OM-21)
RWCFCRPRFCVCV                  (SEQ ID NO:21);

(OM-22)
LCXCRRRXCVCV (X = Cha)         (SEQ ID NO:22);

(OM-23)
RGGRLCYCRRRFCVC                (SEQ ID NO:23);

(OM-24)
LCYTRRRFTVCV                   (SEQ ID NO:24);

(OM-25)
RRCYCRRRFCVCVGR                (SEQ ID NO:25);

(OM-26)
RKCTCRRRFCVCV*                 (SEQ ID NO:26);

(OM-27)
RXRLCYCRZRFCVCV (X = Cha)      (SEQ ID NO:27);
                (Z = MeGly)

(OM-28)
RGWRLCYCRGRXCVCV (X = Cha)     (SEQ ID NO:28);

(OM-29)
RGLRXCYCRGRFCVCVGR (X = Cha)   (SEQ ID NO:29);

(OM-30)
RGWRGCYKRGRFKGCVGR             (SEQ ID NO:30);

(OM-31)
RGWRGCYCRXRFCGC (X = MeGly)    (SEQ ID NO:31);

(OM-32)
RGGLCYCRGRFCVCVGR              (SEQ ID NO:32);

(OM-33)
RLLRLCYCRXRFCVCVGR (X = MeGly) (SEQ ID NO:33);

(OM-35)
RGWRLCYCRGRFCVCVGR             (SEQ ID NO:35);

(OM-40)
WLXYXRRRFCVCV                  (SEQ ID NO:40);

(OM-41)
RGGGLCYARGWIAFCVCVGR           (SEQ ID NO:41);

(OM-42)
LCYCRRRFCVCVF                  (SEQ ID NO:42);

(OM-43)
RLCYCRPRFCVCV                  (SEQ ID NO:43); and (OM-44)
RLCACRGRACVCV                  (SEQ ID NO:44),
``` wherein peptides denoted with * are acid forms and all others are amide forms.

2. The method of claim 1, wherein said peptide is in the native form.

3. The method of claim 1, wherein said antimicrobial peptide is administered at a concentration of about 0.001% (w/w) to 2.5% (w/w).

4. The method of claim 1, wherein said antimicrobial peptide is administered at a concentration of about 0.005% (w/w) to about 0.75% (w/w).

5. The method of claim 1, wherein said antimicrobial compound is administered at a concentration of about 0.03% (w/w) to about 0.3% (w/w).

6. The method of claim 1, wherein said antimicrobial peptide is administered in the form of a gel-like pharmaceutical formulation, said formulation comprising about 0.005% (w/w) to 2.5% (w/w) antimicrobial peptide, about 0.1% (w/w) to 10% (w/w) water-soluble gelling agent and about 0.1% to 20% humectant.

7. The method of claim 1, wherein the pharmaceutical formulation further includes about 0.1% (w/w) to 10% (w/w) sweetening agent.

8. The method of claim 1, wherein the formulation further includes about 0.1% (w/w) to 2% (w/w) antimicrobial preservative.

9. The method of claim 1, in which said peptide is RGGLCYCRGRFCVCVGR-NH$_2$ (SEQ ID NO:3).

10. A composition for topical administration of an antimicrobial peptide, said composition comprising about 0.001% (w/w) to 2.5% (w/w) antimicrobial peptide, about 0.1% (w/w) to 10% (w/w) water-soluble gelling agent, about 0.1% (w/w) to 20% (w/w) humectant, and about 0.1% (w/w) to 10% (w/w) sweetening agent and where said antimicrobial peptide is selected from the group consisting of:

```
(OM-3)
RGGLCYCRGRFCVCVGR              (SEQ ID NO:3);

(OM-4)
RLLRACYCRXRFCVCVGR (X = MeGly) (SEQ ID NO:4);

(OM-6)
RGGGLCYKRGWIKFCVGR             (SEQ ID NO:6);

(OM-7)
RGWGLCYCRPRFCVCVGR             (SEQ ID NO:7);

(OM-8)
RLCYCRPRFCVCVGR                (SEQ ID NO:8);

(OM-10)
LCYCRGRFCVCVGR                 (SEQ ID NO:10);

(OM-11)
RWRLCYCRPRFCVCV                (SEQ ID NO:11);

(OM-12)
RGWRLCYCRPRFCVCVGR             (SEQ ID NO:12);

(OM-13)
RGWRACYCRPRFCACVGR             (SEQ ID NO:13);

(OM-14)
GWRLCYCRPRFCVCVGR              (SEQ ID NO:14);

(OM-15)
XCYCRRRFCVCV (X = Cha)         (SEQ ID NO:15);

(OM-16)
WLXYXRRRFCVCV*                 (SEQ ID NO:16);

(OM-17)
RLCYCRXRFCVCV (X = MeGly)      (SEQ ID NO:17);

(OM-18)
RLCYCRPRFCVCVGR*               (SEQ ID NO:18);

(OM-20)
RXCFCRPRFCVCV (X = Cha)        (SEQ ID NO:20);

(OM-21)
RWCFCRPRFCVCV                  (SEQ ID NO:21);

(OM-22)
LCXCRRRXCVCV (X = Cha)         (SEQ ID NO:22);
```

-continued

```
(OM-23)
RGGRLCYCRRRFCVC              (SEQ ID NO:23);

(OM-24)
LCYTRRRFTVCV                 (SEQ ID NO:24);

(OM-25)
RRCYCRRRFCVCVGR              (SEQ ID NO:25);

(OM-26)
RKCTCRRRFCVCV*               (SEQ ID NO:26);

(OM-27)
RXRLCYCRZRFCVCV (X = Cha)    (SEQ ID NO:27)
                (Z = MeGly)

(OM-28)
RGWRLCYCRGRXCVCV (X = Cha)   (SEQ ID NO:28);

(OM-29)
RGLRXCYCRGRFCVCVGR (X = Cha) (SEQ ID NO:29);

(OM-30)
RGWRGCYKRGRFKGCVGR           (SEQ ID NO:30);

(OM-31)
RGWRGCYCRXRFCGC (X = MeGly)  (SEQ ID NO:31);

(OM-32)
RGGLCYCRGRFCVCVGR            (SEQ ID NO:32);

(OM-33)
RLLRLCYCRXRFCVCVGR (X = MeGly) (SEQ ID NO:33);

(OM-35)
RGWRLCYCRGRFCVCVGR           (SEQ ID NO:35);
```

-continued

```
(OM-40)
WLXYXRRRFCVCV                (SEQ ID NO:40);

(OM-41)
RGGGLCYARGWIAFCVCVGR         (SEQ ID NO:41);

(OM-42)
LCYCRRRFCVCVF                (SEQ ID NO:42);

(OM-43)
RLCYCRPRFCVCV                (SEQ ID NO:43); and (OM-44)
RLCACRGRACVCV                (SEQ ID NO:44),
``` wherein peptides denoted with * are acid forms and all others are amide forms.

11. The composition of claim 10, further including about 0.01% (w/w) to 2% (w/w) antimicrobial preservative.

12. The compositon of claim 11, wherein said antimcirobial preservative is methylparaben or propylparaben or a mixture thereof.

13. The composition of claim 10, wherein said water-soluble gelling agent is a cellulosic material.

14. The composition of claim 13, wherein said cellulosic material is hydroxypropyl methylcellulose.

15. The composition of claim 10, wherein said humectant is sorbitol.

16. The composition of claim 10, in which said peptide is RGGLCYCRGRFCVCVGR-NH$_2$ (SEQ ID NO:3).

* * * * *

UNITED STATES PATENT AND TRADEMARK OFFICE
CERTIFICATE OF CORRECTION

PATENT NO.    : 6,025,326
DATED         : February 15, 2000
INVENTOR(S)   : Steinberg et al.

It is certified that error appears in the above-identified patent and that said Letters Patent is hereby corrected as shown below:

Title page,
Item [62], Related U.S. Application Data,
Lines 1-5, should read -- Continuation-in-part of application No. 08/690,921 Aug. 1, 1996, abandoned, which is a continuation-in-part of application No. 08/649,811, May 17, 1996, abandoned, which is a continuation-in-part of application No. 08/562,346, Nov. 22, 1995, abandoned. --

Column 1,
Line 19, "U.S. Pat. No. 5,708,154", should read -- U.S. Pat. No 5,708,145 --
Line 26, "U.S. Ser. Nos. 08/960,921", should read -- U.S. Ser. Nos. 08/690,921 --

Signed and Sealed this

Second Day of September, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,025,326 | Page 1 of 1 |
| APPLICATION NO. | : 08/752853 | |
| DATED | : February 15, 2000 | |
| INVENTOR(S) | : Deborah A. Steinberg et al. | |

It is certified that error appears in the above-identified patent and that said Letters Patent is hereby corrected as shown below:

Col. 1, under the title, please insert:

--Statement of Rights to Inventions Made Under Federally Sponsored Research

This invention was made with Government support of Grant No. AI022839 awarded by the National Institutes of Health. The Government has certain rights in this invention.--

Signed and Sealed this

Twenty-sixth Day of May, 2009

JOHN DOLL
*Acting Director of the United States Patent and Trademark Office*